(12) United States Patent
Kawamura et al.

(10) Patent No.: US 8,147,406 B2
(45) Date of Patent: Apr. 3, 2012

(54) BIOLOGICAL INFORMATION UTILIZATION SYSTEM, BIOLOGICAL INFORMATION UTILIZATION METHOD, PROGRAM, AND RECORDING MEDIUM

(75) Inventors: Tatsurou Kawamura, Kyotanabe (JP); Akihito Kamei, Yawata (JP)

(73) Assignee: Panasonic Corporation, Osaka (JP)

( * ) Notice: Subject to any disclaimer, the term of this patent is extended or adjusted under 35 U.S.C. 154(b) by 970 days.

(21) Appl. No.: 10/559,723

(22) PCT Filed: Jun. 10, 2004

(86) PCT No.: PCT/JP2004/008466
§ 371 (c)(1),
(2), (4) Date: Dec. 7, 2005

(87) PCT Pub. No.: WO2004/114180
PCT Pub. Date: Dec. 29, 2004

(65) Prior Publication Data
US 2006/0155580 A1    Jul. 13, 2006

(30) Foreign Application Priority Data
Jun. 18, 2003  (JP) .................................. 2003-173254

(51) Int. Cl.
*A61B 5/00*    (2006.01)
(52) U.S. Cl. .......................................... 600/300; 705/3
(58) Field of Classification Search .................. 600/300, 600/301; 128/903–905, 920
See application file for complete search history.

(56) References Cited

U.S. PATENT DOCUMENTS

| | | | |
|---|---|---|---|
| 5,410,471 A * | 4/1995 | Alyfuku et al. | ............... 600/300 |
| 5,785,650 A | 7/1998 | Akasaka et al. | |
| 6,059,724 A | 5/2000 | Campell et al. | |
| 6,221,009 B1 | 4/2001 | Doi et al. | |
| 6,231,519 B1 * | 5/2001 | Blants et al. | ................... 600/300 |
| 6,524,239 B1 * | 2/2003 | Reed et al. | ..................... 600/300 |
| 6,572,564 B2 * | 6/2003 | Ito et al. | ......................... 600/300 |

(Continued)

FOREIGN PATENT DOCUMENTS

EP    0 558 975    2/1993

(Continued)

OTHER PUBLICATIONS

Infectious Diseases Weekly Report (IDWR), Week 9, Feb. 25 to Mar. 3, 2002, with English translation of p. 4.

(Continued)

*Primary Examiner* — Henry M Johnson, III
*Assistant Examiner* — Kai Rajan
(74) *Attorney, Agent, or Firm* — Wenderoth, Lind & Ponack, L.L.P.

(57) ABSTRACT

In a vital data utilization system (100), measurement systems (110) include a measurement unit (111) measuring the vital data of subjects, a clock unit detecting each measurement time at which vital data is measured and a communication unit (112) sending the vital data including measurement time to a server (120). Further, a server (120) includes a communication unit (121) receiving pieces of vital data from measurement systems (110), a vital data storage unit (126) in which vital data is stored, a value-added information making unit (123) making the value-added information indicating the geographical distribution of the vital data or the changes over time of the geographical distributions of the vital data based on vital data stored in the vital data storage unit (126) and a communication unit (121) providing the made value-added information to the measurement systems (110) and the PCs of service destinations.

23 Claims, 17 Drawing Sheets

U.S. PATENT DOCUMENTS

| | | | |
|---|---|---|---|
| 6,612,986 B2 | 9/2003 | Doi et al. | |
| 2001/0009972 A1 | 7/2001 | Doi et al. | |
| 2002/0013520 A1 | 1/2002 | Okamoto | |
| 2002/0147613 A1* | 10/2002 | Kennard et al. | 705/1 |
| 2003/0014283 A1 | 1/2003 | Iwano et al. | |
| 2003/0135394 A1* | 7/2003 | Padron et al. | 705/3 |
| 2003/0163351 A1* | 8/2003 | Brown et al. | 705/2 |

FOREIGN PATENT DOCUMENTS

| | | |
|---|---|---|
| EP | 0 958 778 | 11/1999 |
| JP | 5-228116 | 9/1993 |
| JP | 6-215011 | 8/1994 |
| JP | 08-292939 | 11/1996 |
| JP | 9-319451 | 12/1997 |
| JP | 10/028678 | 2/1998 |
| JP | 10/124601 | 5/1998 |
| JP | 10/248817 | 9/1998 |
| JP | 2001-67403 | 3/2001 |
| JP | 2001-067403 | 3/2001 |
| JP | 2001-137199 | 5/2001 |
| JP | 2001-275997 | 10/2001 |
| JP | 2002-189722 | 7/2002 |
| JP | 2002-311158 | 10/2002 |
| JP | 2003-067506 | 3/2003 |
| JP | 2003-141260 | 5/2003 |
| WO | 98/02086 | 1/1998 |
| WO | 99/44162 | 9/1999 |
| WO | 99/63886 | 12/1999 |
| WO | 01/29688 | 4/2001 |
| WO | 01/73616 | 10/2001 |
| WO | 02/07025 | 1/2002 |
| WO | 03/048725 | 6/2003 |
| WO | 2004/114181 | 12/2004 |

OTHER PUBLICATIONS

Supplementary European Search Report issued Oct. 21, 2010 in corresponding EP Application No. 04 74 6007.

* cited by examiner

BIOLOGICAL INFORMATION UTILIZATION SYSTEM, BIOLOGICAL INFORMATION UTILIZATION METHOD, PROGRAM, AND RECORDING MEDIUM

TECHNICAL FIELD

The present invention relates to a vital data utilization system for processing subjects' vital data collected via a communication network and providing value-added information and a vital data utilization method in the vital data utilization system, and also relates to a program for causing a computer to execute main processing in the vital data utilization system according to the vital data utilization method of the present invention and a recording medium in which the program is recorded.

BACKGROUND ART

Health care supporting systems and services where (i) an individual obtains individual vital data at home in order to utilize the vital data for individual health care and sends the obtained data to a medical facility and the like, and (ii) the medical facility and the like processes and describes the information so that the individual and/or the client can understand the data and sends them to the individual and/or the client.

FIG. 1 is a diagram showing the information flow in a conventional health care supporting system. In the conventional health care supporting system like this, as shown in FIG. 1, value-added information made of only one subject's vital data is provided to a subject, or a contractor who is a directly interested party of the subject, for example, his/her guardian, employer or the like. In other words, in the conventional health care supporting system, the focus is placed on that, as soon as abnormality is detected in individual vital data, the abnormality is immediately notified to the subject and/or the contractor.

The above-mentioned features are described in the Japanese Laid-Open application No. 2001-137199 publication.

However, if not only an individual utilizes his/her vital data for health care but also information indicating health condition of the whole society that is made based on subjects' vital data including other people can be utilized, health care supporting systems and services can become socially more useful. For example, the epidemic of an infection such as an influenza or food poisoning can be anticipated by judging from the increase in the rate of subjects with a fever. In the case where a countermeasure for it is taken early, more effective health care can be realized. If a public institution or the like takes this countermeasure, it is effective for preventing the epidemic from becoming wide spread.

An object of the present invention is, taking into consideration a new need like mentioned above, to provide a vital data utilization system, method, program and recording medium that socially contribute more.

DISCLOSURE OF INVENTION

In order to achieve the above-mentioned object, the vital data utilization system, of the present invention, includes: a server; a receiving apparatus; and measurement instruments, in the system, the server, the receiving apparatus and the measurement instruments are connected to each other via a communication network, each of the measurement instruments has: a vital data measurement unit for measuring vital data of a subject; a clock unit for detecting measurement time at which the vital data is measured; and a sending unit for sending, to the server, a set of information including the measured vital data and the measurement time, the server has: a receiving unit for receiving, from the measurement instruments, sets of information, one of which being the set of information; a storage unit for holding the sets of information; a database making unit for storing the received sets of information into the storage unit and for making a database; a value-added information making unit for computing the vital data of subjects stored in the database and the respective measurement time in an associated manner and for making value-added information indicating changes over time of the vital data of subjects; and a value-added information providing unit for providing the receiving apparatus with the made value-added information, and the receiving apparatus has: an output unit for receiving the value-added information provided by the value-added information providing unit, for outputting, by presenting, the value-added information.

Therefore, with the present invention, the server apparatus can make the value-added information that indicates changes over time of vital data based on sets of vital data that have already been measured in measurement instruments and the respectively corresponding measurement time and provide the value-added information that is made based on the sets of vital data of subjects to the receiving apparatus.

Also, in a first aspect of the present invention, in the vital data utilization system, the sending unit further adds, to respective sets of information, identification information for identifying a corresponding measurement instrument or subject and sends the respective sets of information including the identification information to the server, the database making unit makes individual databases where the sets of information for respective measurement instruments or subjects are stored based on the identification information, and the value-added information making unit calculates differential values between the vital data included in the sets of information that are stored in the individual databases and previously-set standard values of the vital data, averages the calculated differential values concerning the subjects who satisfy a predetermined condition in a predetermined time segment, and makes value-added information indicating changes over time of average values of the differential values concerning the subjects.

Here, in the case of making a setting by which vital data are sent to the server apparatus within a fraction of a second from the time the respective vital data are measured, the time when the server received vital data may be regarded as the corresponding measurement time. In this case, the information on the time is stored in the server apparatus.

As described up to this point, with the present invention, the server apparatus placed at the service provider collects vital data of subjects in real time and makes value-added information showing the change in the health status of the whole subjects. Therefore, an individual, a medical institute, a public institute, a company and the like that are the service destination of value-added information can grasp the occurrence and status of, for example, an infection (such as an influenza and food poisoning) by microbes including a virus substantially in real time by referring to this value-added information. This produces an effect that an individual, a medical institute, a public institute, a company and the like become possible to take countermeasures that are more effective and timely for the interest of health care of individuals or the whole society.

DETAILED DESCRIPTION OF THE INVENTION

Embodiments of the present invention will be described below with reference to figures.

First Embodiment

Figure 1:
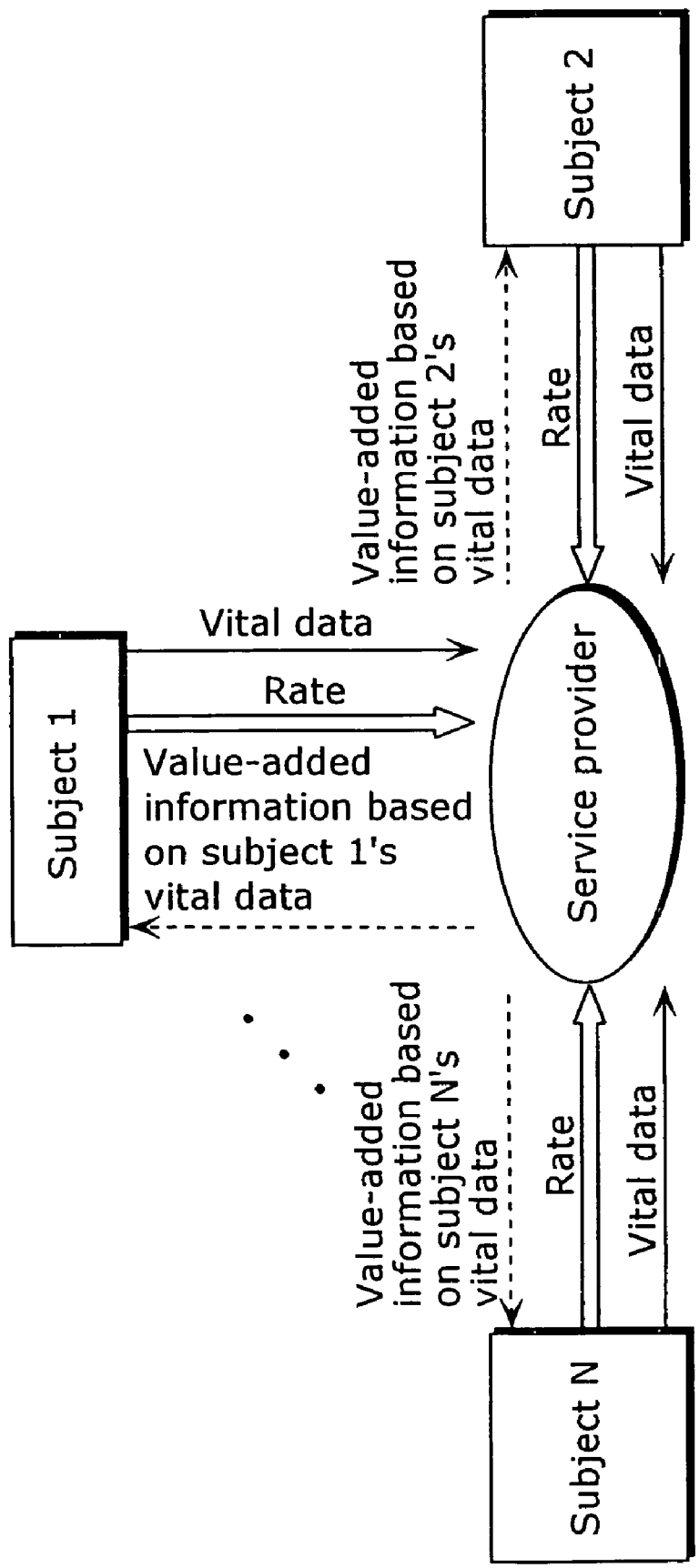
FIG. 1 is a diagram showing information flow in a conventional health care supporting system.
Figure 2:
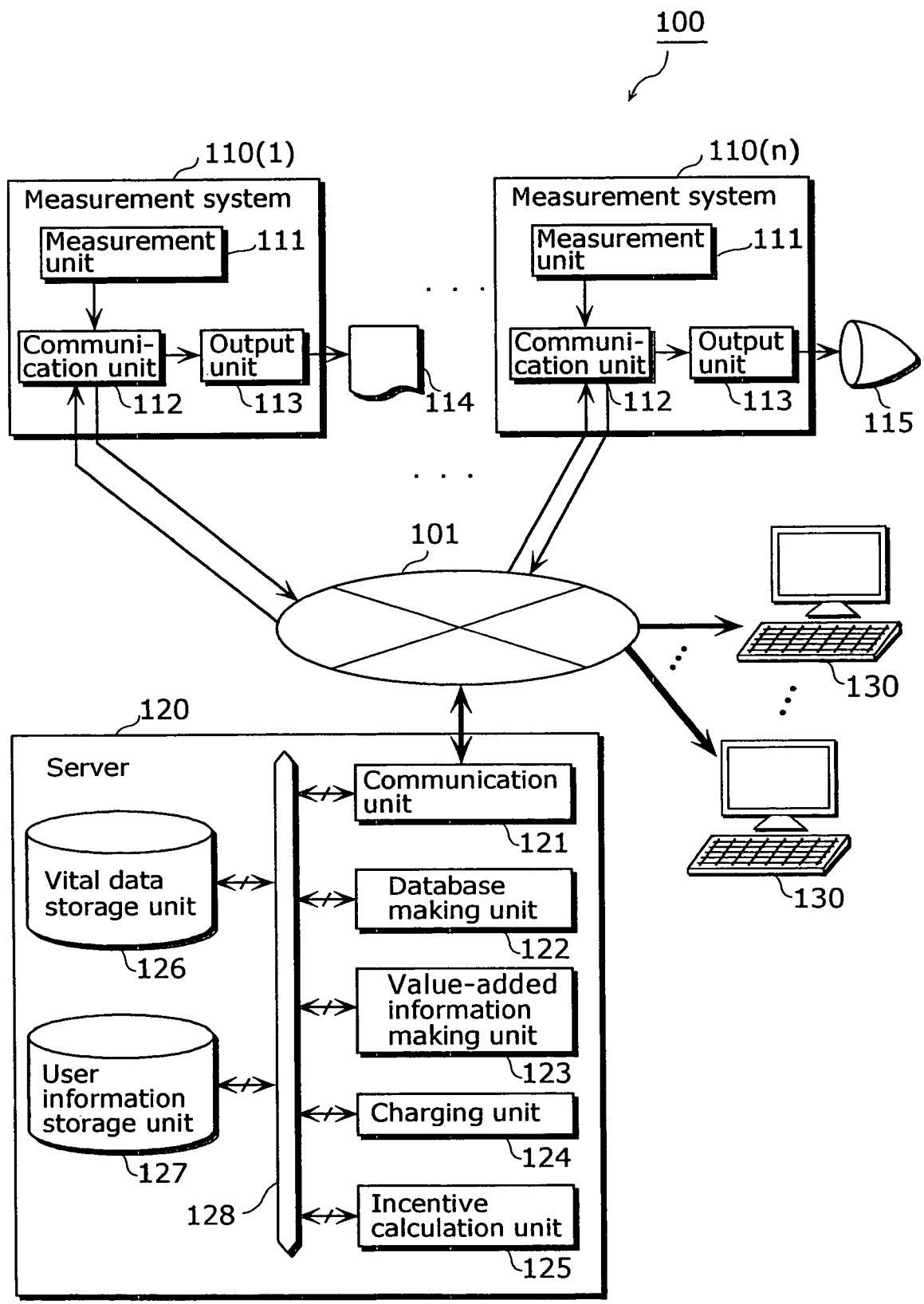
FIG. 2 is a block diagram showing the structure of the vital data utilization system of a first embodiment in the present invention.

The structure of a vital data utilization system of the present embodiment will be described first with reference to mainly FIG. 2. FIG. 2 is a block diagram showing the structure of the vital data utilization system 100 of the first embodiment of the present invention.

The vital data utilization system 100 is a vital data utilization system that makes, in real time, the value-added information indicating the changes over time or the geographical distribution variations of plural vital data based on the subjects' vital data received from plural measurement instruments and distributes the made value-added information to a service destination including the subjects. This vital data utilization system 100 includes a measurement system 110 of 1 to n (n is a natural number) placed at a subjects' home, a server 120 placed at a service provider side and a personal computer 130 placed at the service destination. The measurement system 110, the server 120 and the personal computer 130 are connected to each other via a communication network 101. This enables the service provider of the vital data utilization system 100 to receive the distribution of the value-added information updated in real-time each time the vital data measured in respective measurement systems 110 are received in the server 120.

(1) First, the detailed structure of the measurement system 110 placed at the subject home side will be described.

The measurement system 110 sends the measured vital data of the respective subjects to the server 120 via the communication network 101, and includes a measurement unit 111, a communication unit 112 and an output unit 113. The measurement unit 111 is a processing unit that (i) converts, to digital data that can be processed digitally, measurement values obtained from vital data measurement instruments, for example, a thermometer placed in a home facility such as a toilet and a bed, a urine analyzer, a clock and a blood-pressure meter, and (ii) adds necessary information to the vital data, in order to make vital data including such information to be sent to the server 120. More specifically, the measurement unit 111 adds, to the measurement result by the respective vital data measurement instruments, respective measurement time, vital data identification codes for identifying the kinds of vital data, subject identification codes for identifying a subject inputted by the subject, and residence position information (residence information) of the subject which is previously recorded inside and make vital data. The communication unit 112 previously stores the apparatus identification code of the measurement system 110 inside, adds the apparatus identification code to the vital data made by the measurement unit 111, and sends them to the server 120. The output unit 113 outputs the value-added information distributed from the server 120 to a printer 114, a monitor 115 and the like that are connected externally.

Figure 3:
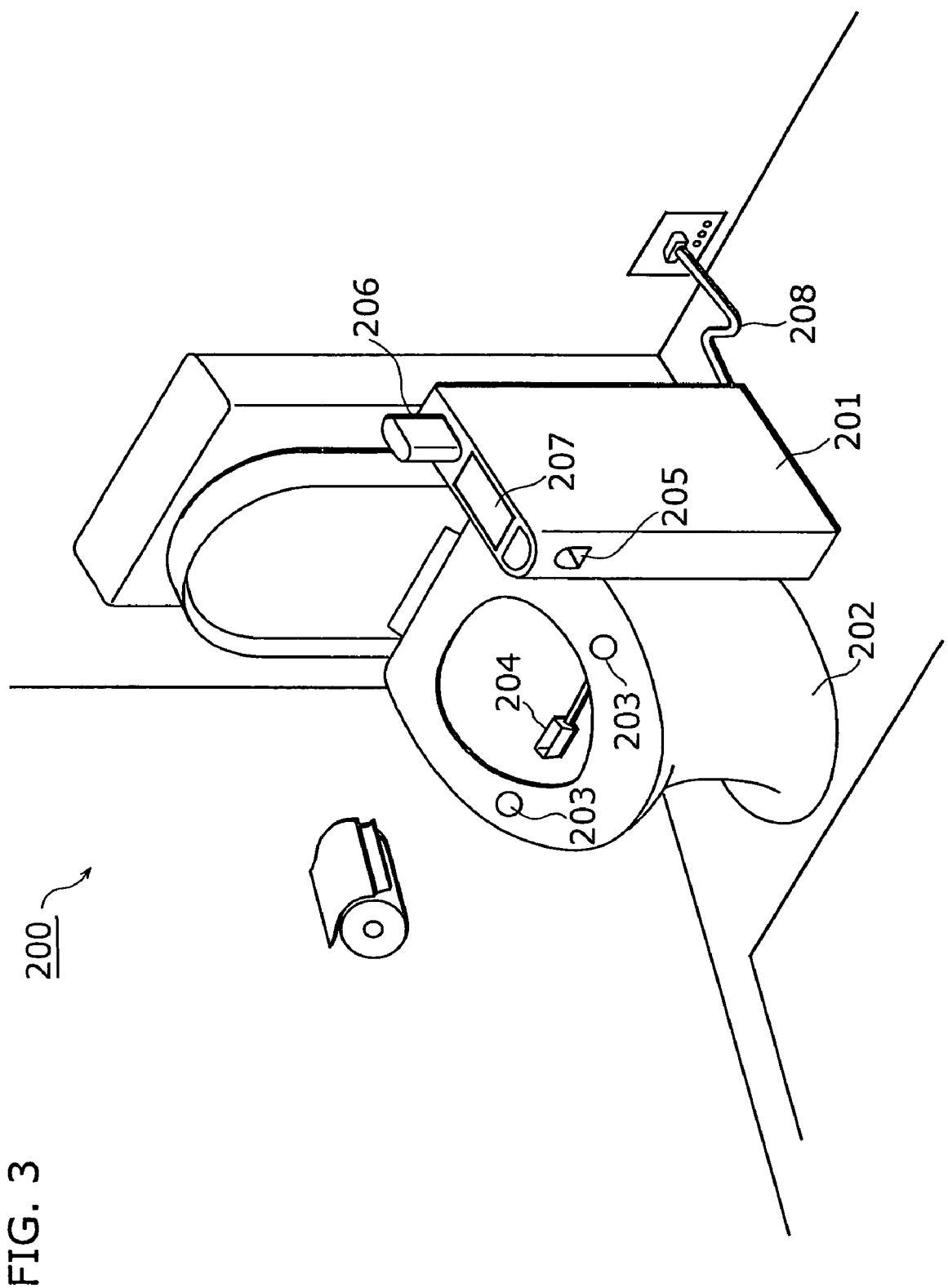
FIG. 3 is a diagram showing the appearance of a toilet apparatus that is an example of the measurement system shown in FIG. 2.

FIG. 3 is a diagram showing the appearance of a toilet apparatus 200 that is an example of how the measurement system 110 shown in FIG. 2 is placed. The toilet apparatus 200 is composed of a measurement instrument body 201 and a toilet bowl 202. In the toilet bowl 202, an electrode pad with a thermosensor 203 for measuring subjects' cardiographs and body temperatures is set on the surface of the toilet bowl contacted by the subjects. Also, inside the toilet bowl 202, a urine and feces taking funnel 204 that samples subjects' urine and feces by sliding. The measurement instrument body 201 includes a finger insertion entrance 205, a blood check apparatus 206, a controller 207, and a control unit that is not shown in figures. The finger insertion entrance 205 is a hole into which a subject inserts his/her finger. Inside the measurement instrument body 201, a blood-pressure meter, a pulsimeter, a meter of accelerated pulse wave velocity and a pulsoxymeter (measurement instrument of oxygen saturation in blood) are placed in order to measure, via the inserted fingers of subjects, blood-pressures, pulses, accelerated pulse wave velocities (the waves showing the increase or the decrease in blood flow amount inside peripheral systems, oxygen saturations and the like). The meter of accelerated pulse wave velocity is a measurement instrument for measuring variations of transmitted/scattered light amount by allowing the light to pass through the fingers. The blood check apparatus 206 where a lancet for taking blood is placed is attached on the measurement instrument body 201 in a detachable way. The blood check apparatus 206 measures the number of white cells, C-reactive protein and the like from a minute quantity of blood obtained by user driving the lancet into his/her skin, and sends the measurement results to the control unit inside the measurement instrument body 201 via infrared or wireless communication. In the control unit, the vital data to be sent of the measurement values received from the respective vital data measurement instruments to be set in a toilet apparatus 200 is made with reference to a table that is previously recorded. The controller 207 includes a display unit for letting the subject know input operations, and operation buttons that receive subject input operations and the like. Such operation buttons include, for example, a button for identifying one subject in the case where plural subjects use one toilet apparatus 200, an operation button for setting the urine and feces taking funnel 204 at an appropriate position by sliding it. The communication cable 208 is a cable for sending, to the communication network 101, the vital data from the communication unit 112 placed at the measurement instrument body 201, and is connected to a telephone circuit and the like.

By using such toilet apparatus 200, the subject inputs his or her identification information by pressing the button for identifying an individual that is placed on the controller 207 first, and next, sits down on the toilet bowl and urinates or defecates. At that time, various sets of vital data are measured using vital data measurement instruments set on the measurement instrument body 201. The measurement unit 111 obtains, for example, individual identification information, measurement time and the like from the controller 207 and a clock of the measurement instrument body 201, and obtains measurement values (the body temperature and the protein concentration in urine) of the subject from the thermometer and the urine analyzer that are placed in the toilet apparatus 200, and makes his/her vital data. The communication unit 112 sends, to the server 120, the measurement result (vital data) by the measurement unit 111 and the position information of the subject's residence (residence information). The output unit 113 obtains the value-added information made by the server 120 via the communication unit 112 and outputs it to an external printer 114 or an external monitor 115, therefore, the subject can inspect the value-added information printed by the printer 114 or displayed on the monitor 115.

The toilet apparatus 200 structured like this starts measuring vital data by detecting a weight put on its toilet bowl at the time when the subject uses the toilet apparatus. For example, by setting the program of the measurement unit 111 so that it can automatically start measuring at the time of detecting that the user urinates or defecates after waking up in the morning, the vital data measurement instrument that is set in the toilet bowl 202 can automatically measure subject's body temperature, cardiograph, feces viscosity, protein concentration in urine and the like and send the vital data indicating the measurement results to the server 120. This produces a merit that (i) measurements are performed at the time when the subject's vital conditions are stable or at a predetermined measurement time, (ii) the subject is prevented from forgetting to perform the measurement, and that (iii) vital data can be obtained periodically and continuously. Note that the measurements of vital data in the measurement system 110 may be started by the subject operating the controller 207 and inputting the indication of starting individual authentication and measurement.

Figure 4:
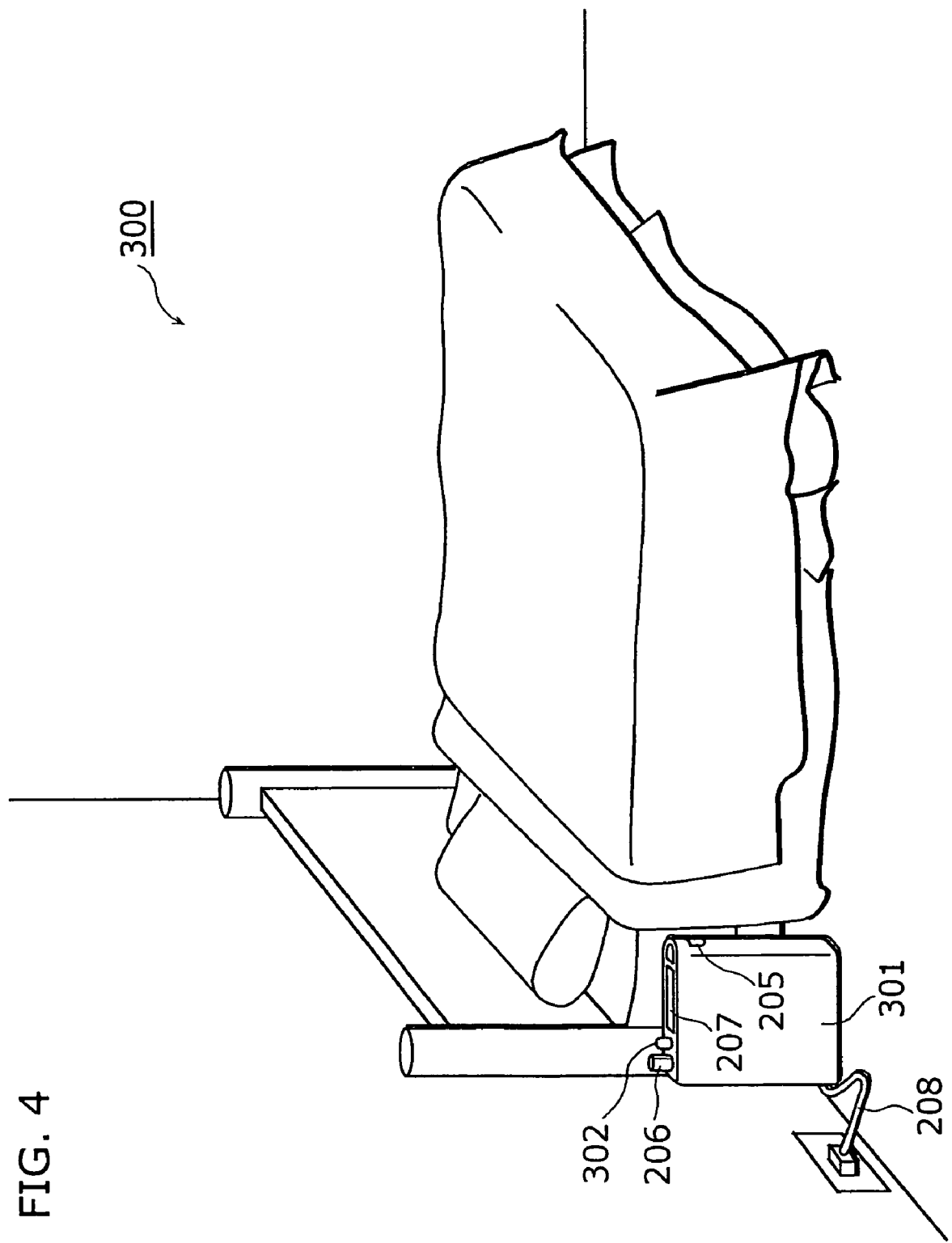
FIG. 4 is a diagram showing the setting example where the measurement instrument body is set on a bed.

On the other hand, a thermometer or vital data measurement instruments that measure blood-pressure, pulse, cardiograph or oxygen saturation in blood respectively are effective when measuring such vital data periodically and continuously also in the case where they are set beside a bed. FIG. 4 is a diagram showing the setting example 300 where the measurement instrument body 301 is set beside the bed. In the figure, since the same measurement instruments such as the vital data measurement instrument shown in FIG. 3 have already been described, the same reference numbers are assigned to them and descriptions on them will be omitted. A thermometer and a cardiograph 302 are further placed to the measurement instrument body 201 shown in FIG. 3 to become the measurement instrument body 301. The thermometer and the cardiograph 302 are attached to the measurement instrument body 301 in a detachable way likewise the blood check apparatus 206, and the measurement results are sent to the control unit inside the measurement instrument body 301 via the infrared or a wireless communication.

(2) Next, the detailed structure of the server 120 in the service provider side that provides the service will be described with reference to FIG. 2.

The server 120 makes the value-added information from the plural subjects' vital data sent from plural measurement systems 110. It is realized in a computer system, and includes a communication unit 121, a database making unit 122, a value-added information making unit 123, a charging unit 124, an incentive calculation unit 125, a vital data storage unit 126, a user information storage unit 127 and a bus 128. The communication unit 121 receives vital data from the respective measurement systems 110 via the communication network 101, and distributes, to the respective personal computers 130 and the measurement systems 110 that are the service destinations, the value-added information made by the value-added information making unit 123. Note that the personal computers 130 that are the service destinations include a communication unit, which is not shown, for receiving the value-added information, bills and the like from the server 120, and the personal computers 130 are connected to a monitor for displaying the received value-added information, bills and the like, and a printer for printing the received value-added information, bills and the like. The database making unit 122 makes the database of vital data that change over time and store the database into the vital data storage unit 126, the vital data being received by the communication unit 121. The value-added information storage unit 123 makes the value-added information A indicating the changes over time of the vital data of all the subjects and the value-added information B that is the position distribution information of the vital data based on the residence information of all the subjects, based on the vital data database made by the database making unit 122. The charging unit 124 calculates the rate charged on the value-added information destination depending on the contract coverage for each user stored in the user information storage unit 127. The incentive calculation unit 125 calculates the points of incentives to the subjects who provided the vital data periodically and continuously. The incentives are, for example, the rights for receiving the discount rate for such value-added information, or for receiving the discount or trade for a test reagent. Especially, the test reagents and the like used by the measurement unit 111 further encourages measurements of vital data, their encouragement effect is great and thus they are particularly effective. Here, for example, buffer solutions or antibody solutions that are used in the measurement by the immunonephelometry are listed as test reagents. The vital data storage unit 126 is realized by the large capacity storage apparatus such as a hard disc and stores the vital data database made by the database making unit 122. The user information storage unit 127 is realized by the large capacity storage unit such as a hard disc, and stores various kinds of tables used for a user information database made of individual information, contract coverage, charging information and the like for each user. The data stored in the user information storage unit 127 is sequentially updated by the input operation unit in the server 120 that is not shown in any figure, the charging unit 124 and the incentive calculation unit 125. The vital data storage unit 126 and the user information storage unit 127 are shown as different storage units in FIG. 2. However, actually, different storage units are not always needed, respective databases need to be stored in different storage region.

Figure 5:
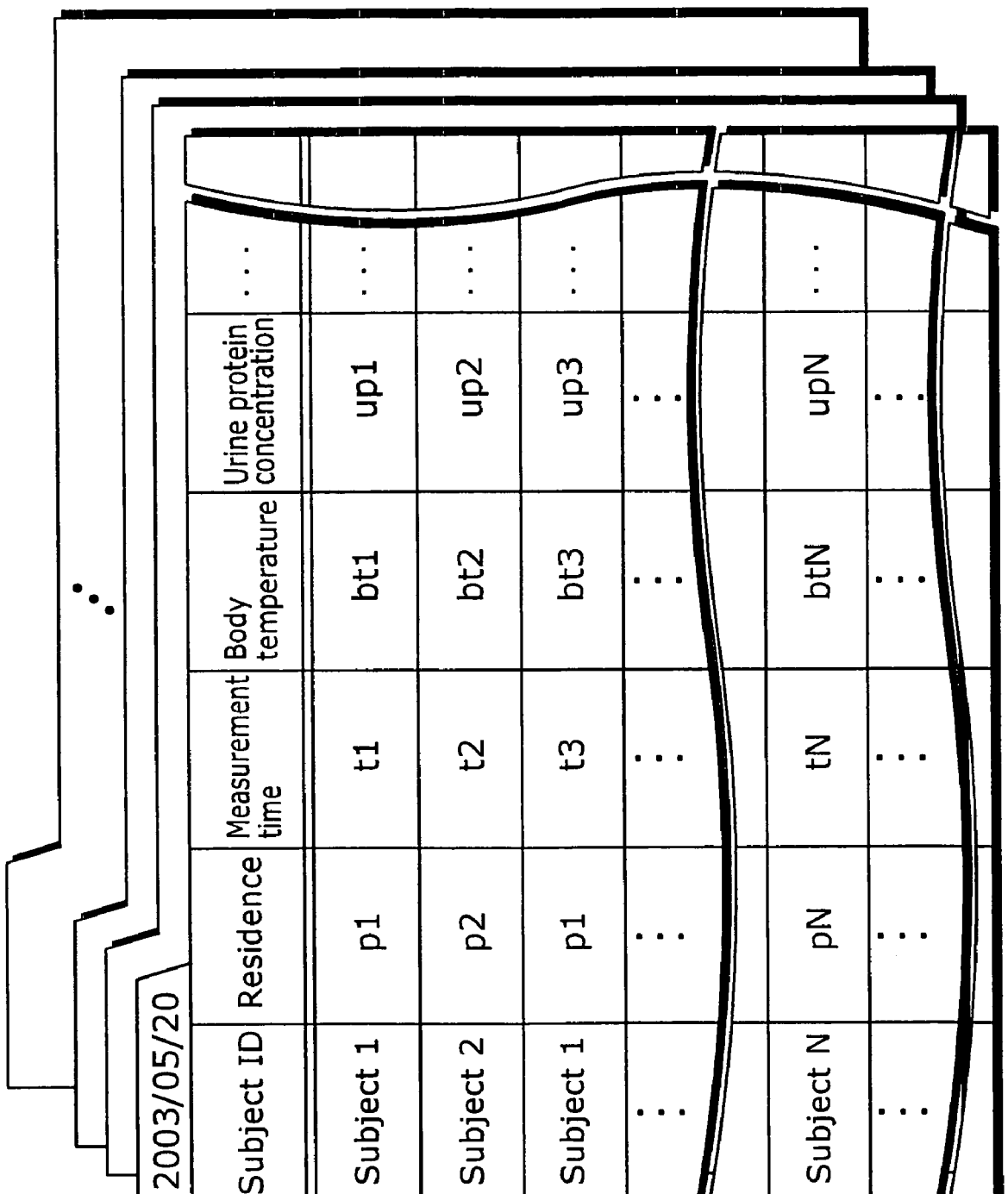
FIG. 5 is a diagram showing an example of vital data database made by a database making unit.

FIG. 5 is a diagram showing one example of vital data database made by the database making unit 122. The database making unit 122 stores the received vital data (individual information, body temperature, protein concentration in urine) of plural subjects, respective measurement time and residence, and makes the vital data database shown in FIG. 5. The database format of the embodiment shown in FIG. 5 includes articles of (i) subject N (N is a natural number) as the subject ID, (ii) residence pN, (iii) measurement time tN as the time, date, month and year of the measurement, (iv) body temperature btN, (v) protein concentration in urine upN and the like, and these articles are described like, for example, (i) subject N, (ii) residence "house number, town, city and prefecture", measurement time "7:12 Feb. 27, 2003", body temperature "38.54° C., protein concentration in urine "28 mg/dl". These sets of vital data are stored in the vital data storage unit 126 in the order of measurement time.

The respective operations performed in the server 120 structured like mentioned above will be described below with reference to FIG. 6, FIG. 7 and FIG. 8.

Figure 6:
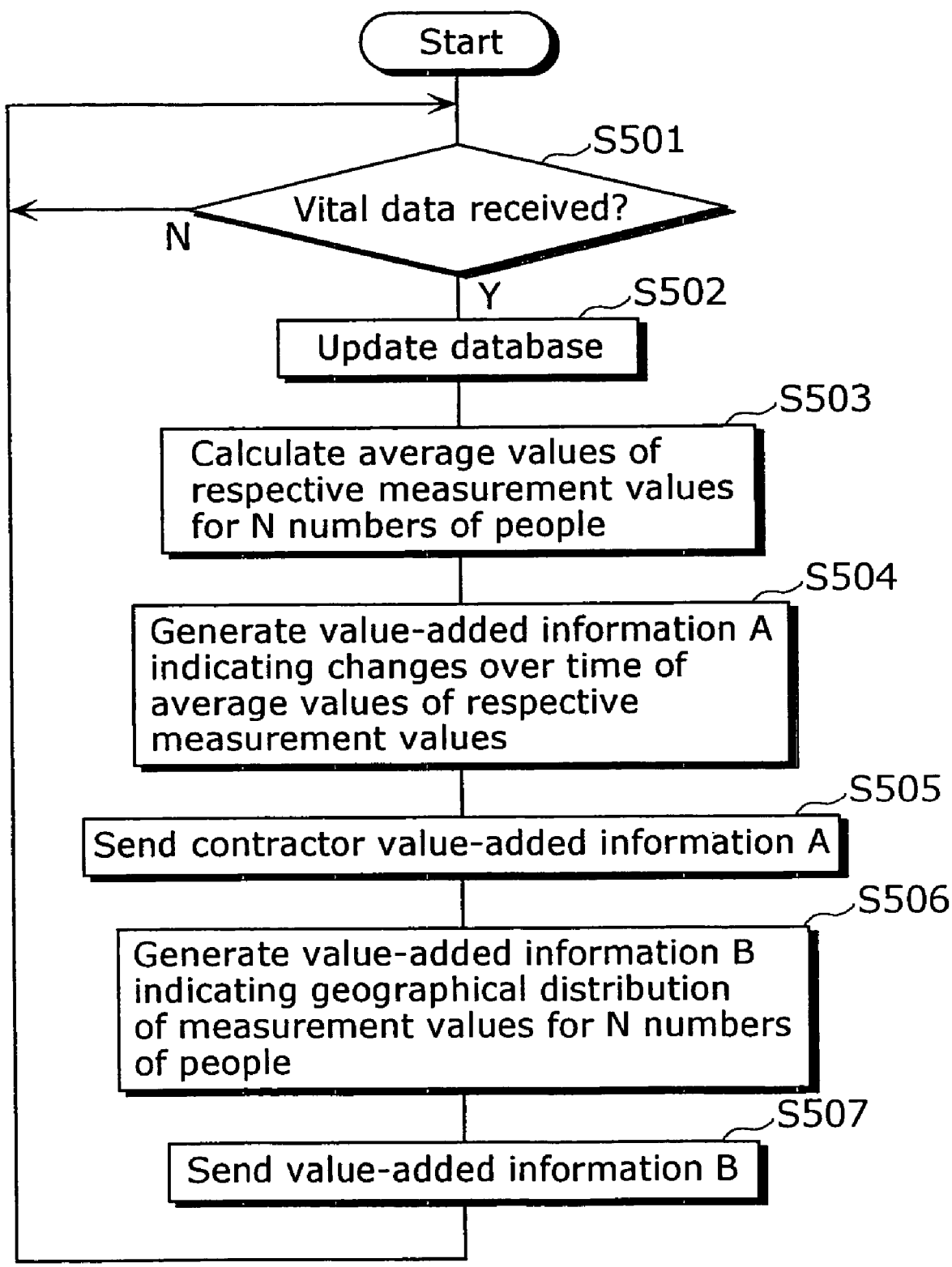
FIG. 6 is a flow chart showing the operation in the value-added information making processing by each server shown in FIG. 2.
Figure 7:
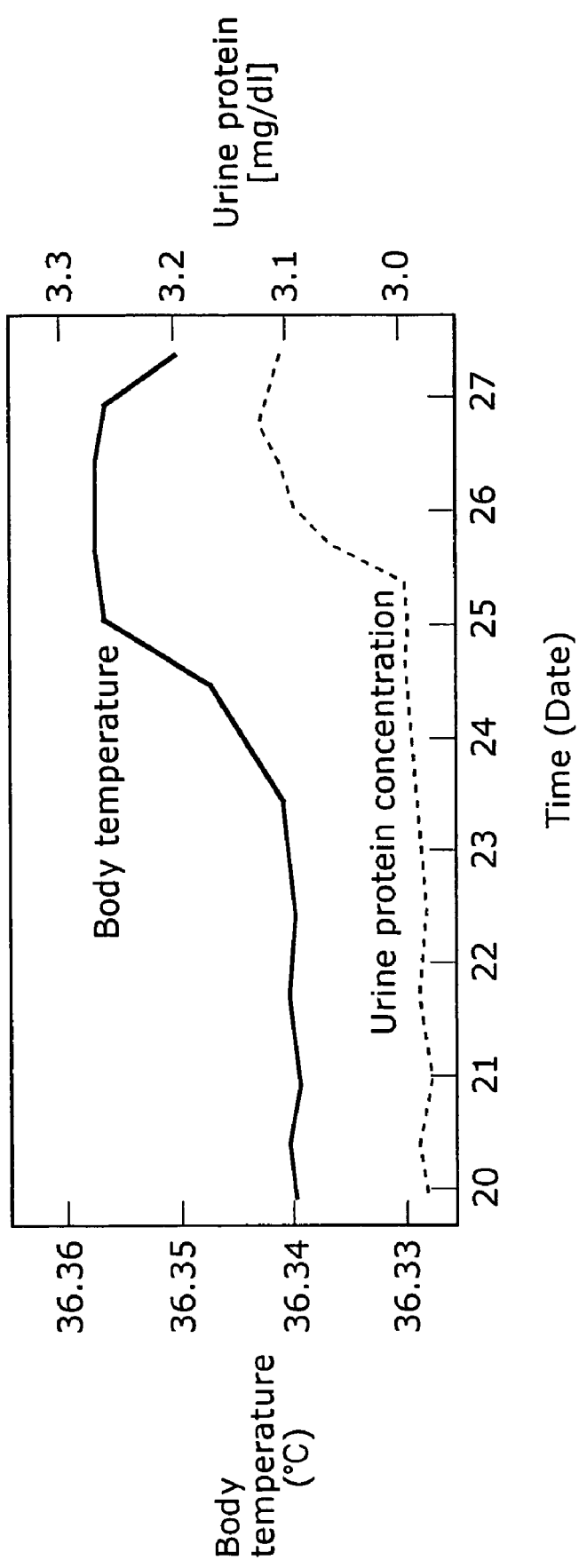
FIG. 7 is a graph showing an example of the value-added information A made by the value-added information making unit shown in FIG. 2.

FIG. 6 is a flow chart showing the operation in the value-added information making processing of the respective units of the server 120 shown in FIG. 2. FIG. 7 is a graph showing one example of the value-added information A made by the value-added information making unit 123 shown in FIG. 2. FIG. 8 is a diagram of one example of the value-added information B made by the value-added information making unit 123 shown in FIG. 2. First, the communication unit 121 in the server 120 waits for receiving the vital data sent from the measurement system 110 (S501). The communication unit 121 sends the received vital data to the database making unit 122 upon receiving the vital data from each of the 1 to n measurement systems 110. The database making unit 122 stores the vital data obtained from the communication unit 121 in the vital data database in the order of measurement time (S502). When the vital data database in the vital data storage unit 126 is updated with new vital data, the value-added information making unit 123, for example, calculates the average values of measurement articles of the received and stored vital data for each prefecture, city, town or village per 12 hours (S503), makes the value-added information A shown in FIG. 7 (S504), and distributes the made value-added information A to a contractor who is the service destination (S505).

The value-added information A of the present invention will be described in detail with reference to FIG. 7. In FIG. 7, the horizontal axis shows time passage and the vertical axis shows body temperature and protein concentration in urine. Here, as to time passage, respective time in a day at which respective sets of vital data are measured are divided into AM (0 o'clock to 12 o'clock) or PM (12 o'clock to 24 o'clock). The vertical axis shows averages of body temperatures and averages of protein concentration in urine of k numbers of subjects (k is a natural number and the same person can be counted twice) in the same prefecture, city, town or village for the divided time zone. In the example shown in the figure, the average value of body temperatures starts increasing from the PM of day 23, reaches the peak in the PM of day 24, and starts decreasing from the AM of day 27. On the other hand, it shows that the average value of the protein concentration in urine starts increasing from the PM of day 25, reaches the peak in the PM of day 26, and starts decreasing from the AM of day 27. Viewing FIG. 7 after the PM of day 27 shows that a cold or the like has started becoming epidemic from day 23 and was settling down on day 27. Also, it shows that average body temperature has started increasing at the time when this value-added information (value-added information A based on the vital data up to the AM of day 24) to the value-added information destination. In this way, the value-added information destination can obtain various merits as will be mentioned below.

First, in the case where the value-added information destination is a medical institute in the area, as it is anticipated that the number of patients will increase from today, it is possible to prepare treatment or eating services accordingly. Also, similar merits can be obtained also in the case where the value-added information destination is a public institute in the area. For example, it is anticipated that the number of absentees will increase in the case where the value-added information destination is a school. Also, in the case where the value-added information destination is a health center or the like, it is possible to take a countermeasure immediately (in a way of prevention) according to this. Also, in the case where the value-added information destination is a service business relating to, somehow or other, health statuses of the residents of an area, for example, in the case of a taxi company, as it is anticipated that the number of passengers going to a health institute or the like will increase, it is possible to use this information in scheduling the dispatch of taxies. Also, for example, in the case where it is a feeding company, it is possible to anticipate the increase in the demand for menus for patients such as rice gruel. In this way, anticipating the change in health status of the whole residents in an area enables providing service industries with great merits. Also, for example, the value-added information destination is a home (including a subject's home), in the case where it is judged that a disease such as a cold or the like is epidemic, preventive measures can be taken such preventive measures which are: putting on a mask as a preventive measure when going out; refraining from going out; and making a child stop going to school. Accordingly, using such information is effective for health care at home. These merits can be realized by making use of this information communication technique of collecting the vital data of the whole subjects in substantially real time via the communication network 101, processing these sets of information, and distributing these processing results in real time.

Next, the value-added information making unit 123 calculates the average values of vital data for respective areas that are minutely divided and makes the value-added information B indicating the geographical distribution of the average values of vital data for the respective areas (S506). The communication unit 121 distributes the made value-added information B to the contractor that is the service destination (S507) and then returns to the processing of step S501. In other words, it waits until it receives next vital data from one of the measurement systems 110. The value-added information B of the present invention will be described in detail below. The value-added information B shown in FIG. 8 is a diagram showing the geographical distribution of the averages of vital data (body temperatures) made based on the vital data database in the vital data storage unit 126. In other words, it is a diagram on which vital data A is mapped. More specifically, it is the diagram where the average values of respective sets of vital data for the respective small areas are calculated and displayed using shading. In FIG. 8, for example, in the case of A area located in the north most part, the average value is low (36.33 to 36.34° C.) and even in the area (there is no difference in average values in the area). On the other hand, in the case of B area and C area, it is known that average values are high in the respective centers of the respective areas and these distributions are uneven. This enables anticipating that an infection is spreading from these centers of the B area and the C area. Further, comparing the changes overtime of the distribution shown in the value-added information B in FIG. 8 enables grasping the trend such as the movement of the epidemic range of the infection. This is greatly useful when a public institute or the like in an area takes various kinds of measures for such infection.

Note that, the above-mentioned first embodiment shows an example where a thermometer and a cardiograph are set on the part such as the toilet bowl of a toilet apparatus 200 that contacts skin in FIG. 3, but the present invention is not limited to the example. For example, by setting measurement instruments for measuring blood pressure, pulse, oxygen saturation in blood and the like other than the above-mentioned thermometer and the cardiograph on the part such as a toilet bowl that contacts skin, it is possible to reduce the labor in measuring these sets of vital data. This is effective in measuring these vital data periodically and continuously. Also, it is possible to set a urine analyzer for measuring glucose concentration in urine and amino acid concentration in urine other than protein in urine. Further, measuring feces viscosity is effective for monitoring an infection such as food poisoning. Also, measuring albumin, globulin, hemoglobin and myoglobin as protein in urine is widely applicable because they easily change depending on daily physical conditions. Here, as a checking method of protein in urine, the immunonephelometry is suitable. With the immunonephelometry, it is possible to specifically detect only a specific protein or a hormone (separating albumin, globulin, hemoglobin and the like) and measure the concentration of each component. Also, it is easy to make apparatuses for the immunonephelometry smaller because, in the immunonephelometry, it is possible to calculate concentration by mixing urine with antibody solution including an antibody that specifically combines with a specific protein or a hormone and by optically measuring the turbidity of the urine. In this way, a specific protein or a hormone can be measured by a comparatively small apparatus using the immunonephelometry, and therefore, the method is especially suitable for monitoring daily health statuses at home.

Also, as an especially effective vital data in grasping an infection, the number of white blood cells and the concentration of C-reactive protein (CPR) are listed. Also, measuring the amount of specific antibody (IgE-RIST) in blood enables knowing the epidemic of pollinosis.

Second Embodiment

In the above first embodiment, the value-added information making unit 123 makes the value-added information A and the value-added information B using the average values of the received sets of vital data. This second embodiment differs from the first embodiment in that value-added information is made using the differences between the respective measurement values and the respectively corresponding standard values of such vital data. The vital data utilization system of this embodiment will be described below with reference to FIG. 9 and FIG. 10. The vital data utilization system of the second embodiment differs from the vital data utilization system 100 of the first embodiment shown in FIG. 2 in that it has a different database making unit 122, a value-added information making unit 123 and a vital data storage unit 126 that are not shown in any figures. The same structural components as the ones shown in FIG. 2 have already been described and descriptions for them will be omitted.

Figure 9:
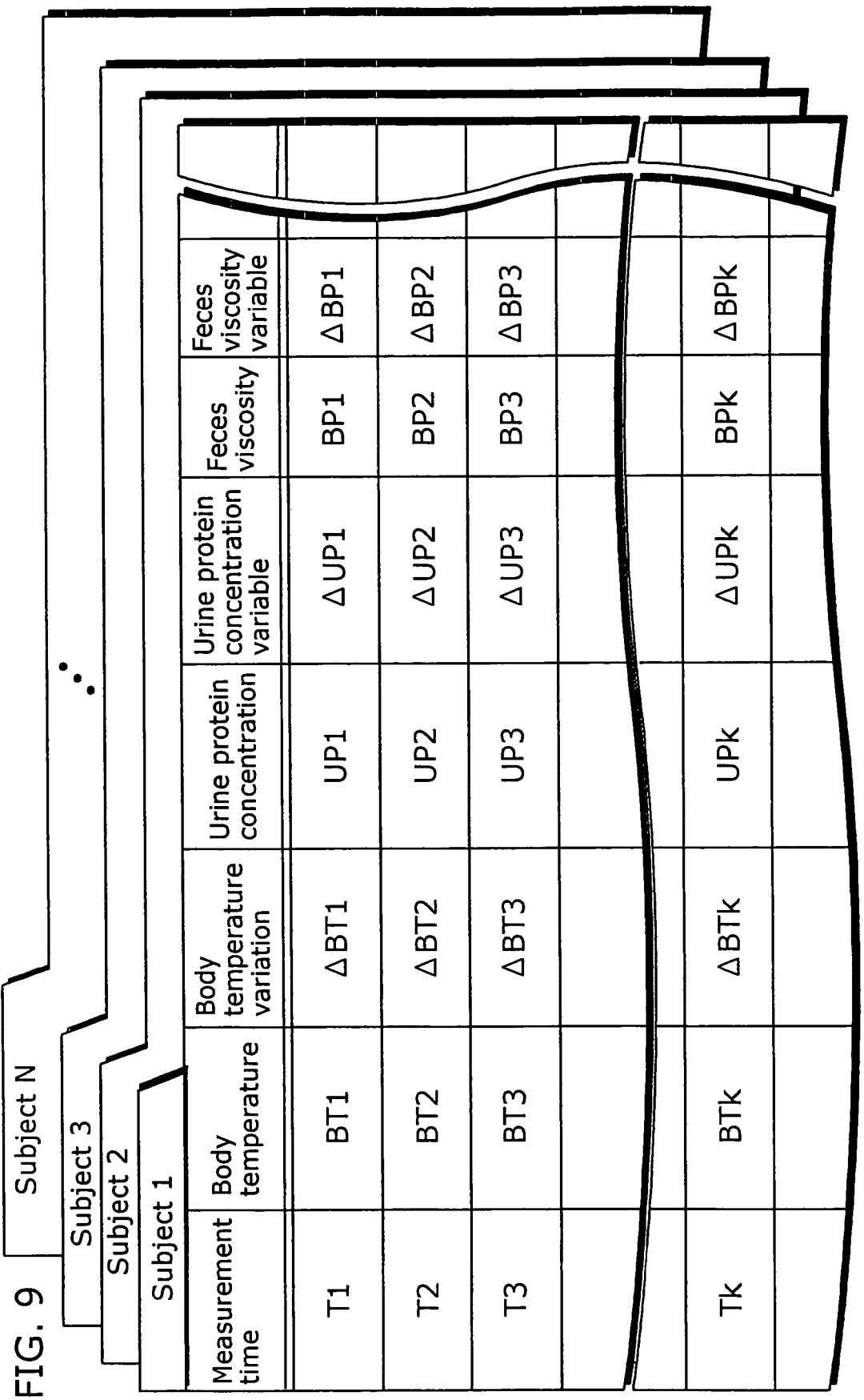
FIG. 9 is a diagram showing an example of individual vital data database made by the database making unit in a second embodiment.

FIG. 9 is a diagram showing one example of individual vital data database made by the database making unit of the second embodiment. As shown in the figure, in the individual vital data database made by the database making unit, sets of vital data from the respective subjects are stored individually, in the order of measurement time. Here, addresses of the respective subjects and the positions where measurement systems are set that are necessary for making such sets of value-added information are obtained from the user information database made in the user information storage unit. In the individual vital data database of the respective subjects, articles such as measurement time Tk, body temperature Btk, body temperature variation $\Delta$BTk, urine protein concentration UPk, urine protein concentration variation $\Delta$ UPk, feces viscosity BPk and feces viscosity variation $\Delta$ BPk will be described.

Figure 10:
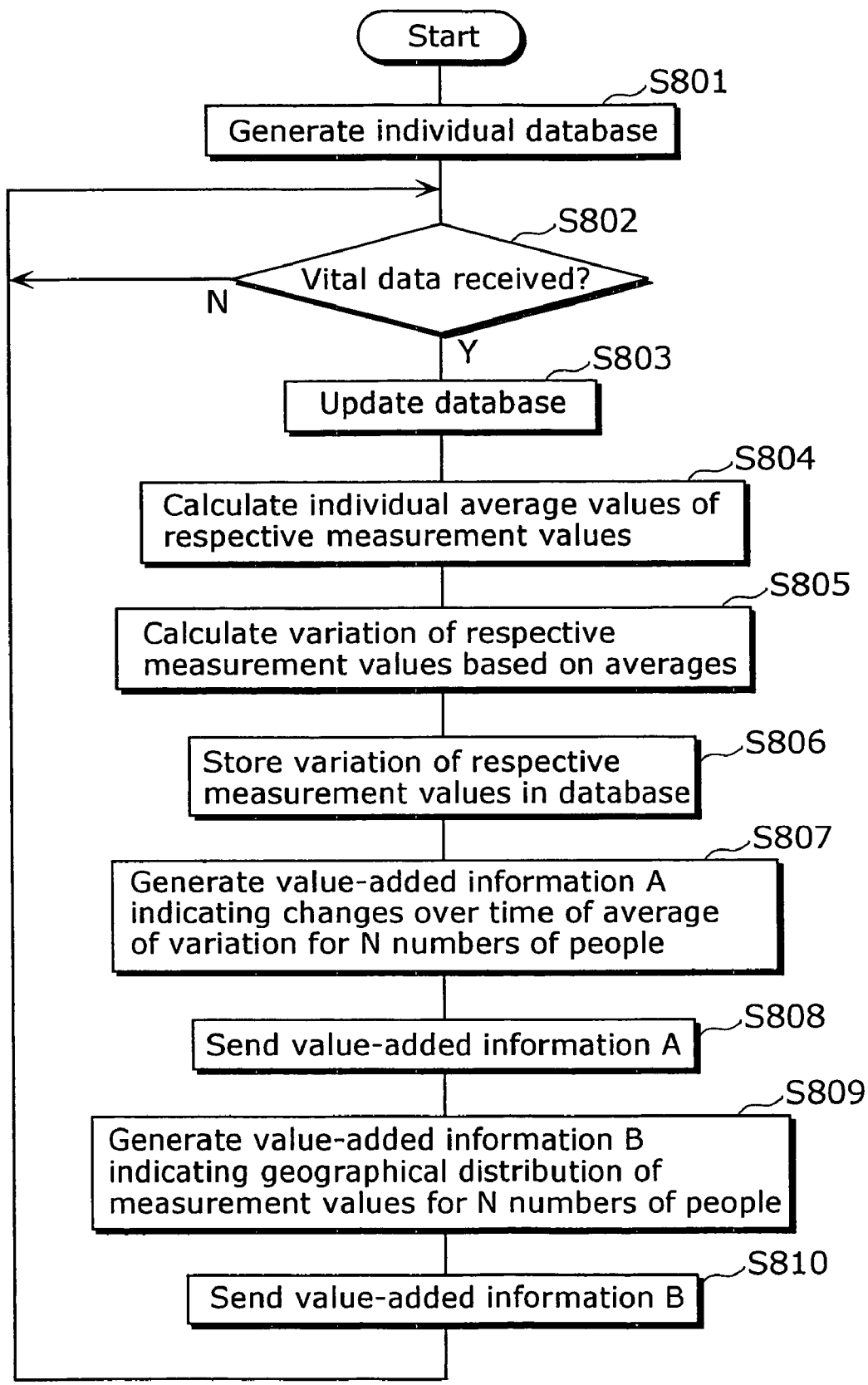
FIG. 10 is a flow chart showing the operation of each unit of the server in the second embodiment.

FIG. 10 is a flow chart showing the operations of each server of the second embodiment. The database making unit of the second embodiment makes individual vital data database in the vital data storage unit first (S801). In the individual database at this stage, the data structure for storing vital data individually is defined. The communication unit 121 waits for receiving such vital data repeating the judgment on whether or not vital data is received from one of the measurement systems 110 (S802). When vital data is received in the communication unit 121 in a waiting state, the database making unit updates the individual vital data database by identifying the subject of the received vital data and storing the received vital data in the storage area for each identified subject (S803). The database making unit identifies the subject of the vital data by referring to the user information stored in the user information storage unit and obtaining the subject ID from the apparatus identification code attached to the vital data. In this way, past vital data of respective subjects are stored individually. Note that variations of measurement values such as body temperature, protein concentration in urine and feces viscosity shown in FIG. 9 are not stored, that is, columns for such sets of vital data remain blank at this time. The value-added information making unit calculates the average values of sets of vital data that are respective measurement values of the respective subjects in a specific past period based on this individual vital data database (S804). Here, the period for calculating past average values of sets of vital data of the respective subjects is, for example, a month during which measurement values experience less variation among the vital data stored in the past. Next, the value-added information making unit calculates the variation between a present measurement value and the past average value by calculating the difference between the latest vital data received in the step S802 and the average value calculated in the step S804 (S805). The value-added information making unit additionally writes the variations of the respectively calculated measurement values into the individual vital data databases shown in FIG. 9 and stores them (S806). Further, the value-added information making unit calculates the average values of variations that are stored respectively for N numbers of people in the respective prefectures, cities, towns or villages, and respectively for a 12-hour duration including the measurement time, and makes the value-added information A indicating the changes over time of the calculated average values (S807). The communication unit 121 distributes the made value-added information A to the contractor that is the service destination of the value-added information A (S808).

Figure 11:
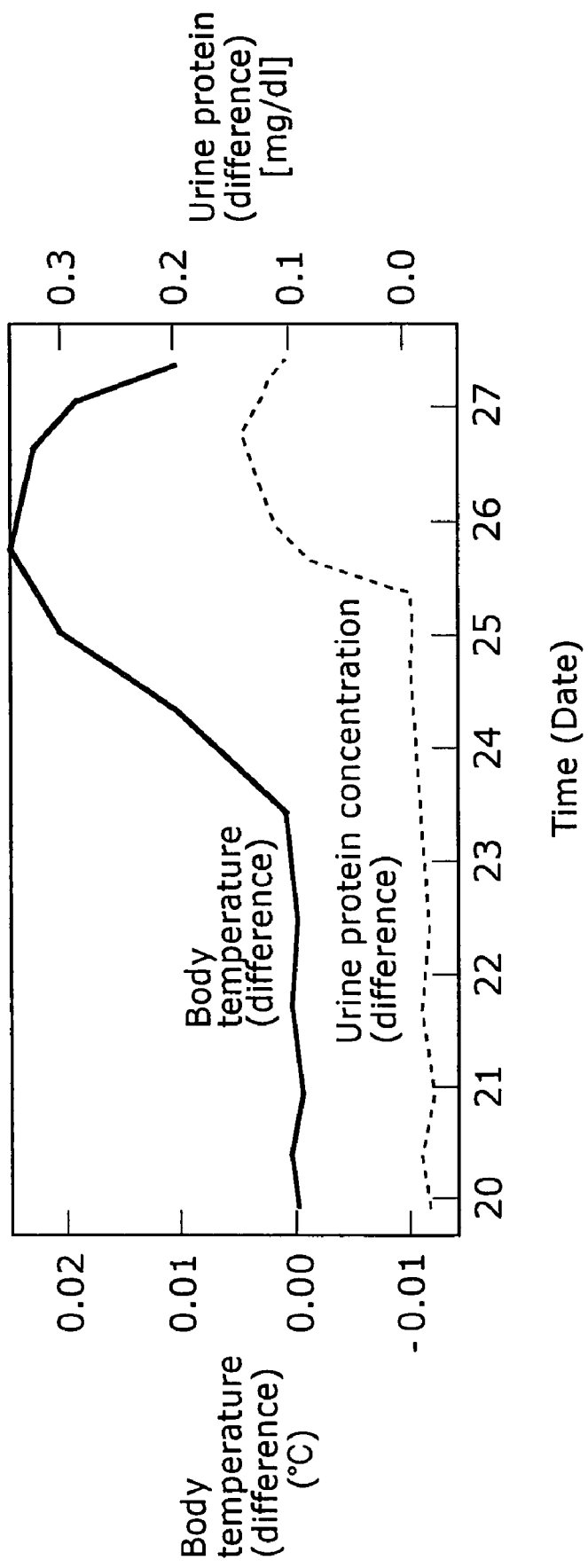
FIG. 11 is a graph showing an example of value-added information A made by the value-added information making unit in the second embodiment.

FIG. 11 is a graph showing one example of the value-added information A made by the value-added information making unit of the second embodiment. In the figure, the horizontal axis shows time and the values for vertical axis show the average values of variations of the body temperature and the protein concentration in urine that can be obtained by taking the average of the subjects' variations from the respective subjects' average values. In the case of body temperature, the value is the average of the subjects' body temperature variations from the respective subjects' average body temperatures. In this way, making use of the differences between the average values of vital data in a specific past period and the measurement values enables reducing the influence of unevenness in the normal values of the respective subjects and indicating the change in the health status of the whole subjects more correctly. For example, in the case where the subjects who have a normal body temperature that is higher than average send his or her vital data (body temperature) at the rate higher than usual, the average value of such subjects' body temperatures seems to be increased. However, it does not indicate a fever caused by an infection or the like. It is difficult to exclude a misjudgment because of individual differences like this using the value-added information A shown in FIG. 7, but the value-added information A shown in FIG. 11 produces the merit of enabling reducing the influence caused by the individual differences.

Further, the value-added information making unit calculates, based on the variations of the respective measurement values stored in the individual vital data databases, the average value of the variations that is stored for N numbers of people in the smaller areas that are further divided and for a 12-hour time duration including the measurement time. Further, it makes the value-added information B showing using shading, for example, the geographical distribution of the calculated averages (S809). The communication unit 121 distributes the made value-added information B to the contractor that is the service destination (S810). After that it returns to the processing in the step S802 and waits until the next vital data is received.

As described up to this point, the value-added information making unit of the second embodiment produces the effect that it is possible to reduce the influence of the differences among individuals who are the subjects and provide the value-added information enabling making a more correct judgment to the service destination of the value-added information in addition to the effect by the value-added information shown in the first embodiment.

Also, in the above-mentioned second embodiment, among the respective subjects' vital data stored in the past, the average value obtained in a specific period during which measurement values are stable is calculated, and value-added information is made, regarding the average value as a normal value, based on the difference between the normal value and the latest measurement value. However, it is possible to make the value-added information A and B based on the difference between the normal value and the latest measurement value after registering the normal values (such as normal body temperatures) of the respective subjects in the individual vital data databases.

Further, the period during which the above-mentioned normal values are calculated may be simply a specific period (such as a month) dating back from the present to a specific time (such as a year ago), or the average value obtained in a specific month in each year. In this case, as all of the subjects are not always healthy in the calculation periods of normal values, the rate of eliminating the individual differences of subjects decreases, but it is possible to reduce the processing load of the value-added information making unit. Also, it is possible to determine the normal value for the respective measurement articles such as body temperature, protein concentration in urine and feces viscosity. In this case, it is impossible to prevent the influence of the individual differences of subjects but possible to reduce the processing load of the value-added information making unit more.

Note that, in the above-mentioned first and second embodiments, the average values of the respective measurement values per 12 hours are obtained as the value-added information A, but the present invention is not limited to this. For example, it is possible to calculate the average values on a time basis such as one hour or a minute basis in the case where the number of subjects are many, or it is possible to calculate the average values on a daily basis such as every day and every other day in the case where the number of subjects are not so many.

Note that it is described that the value-added information A and the value-added information B are distributed to the contractor as soon as each of them is made in the above-mentioned first and second embodiments, but it is possible to distribute them to the contractor after making both of them.

Also, it is described that the average values of vital data are calculated for respective prefectures, cities, towns or villages to which subjects' addresses or the setting positions of the measurement systems 110 belong, and then the value-added information A is made in the above-mentioned first and second embodiments, but the unit may be a block number. Also, geographical units specified using zip codes may be used. Further, the areas that are set freely and have an arbitrary size may be used as such units.

Also, the area for which the average value of the vital data is calculated at the time of making the value-added information B may be the same as the area, which is a geographical unit, for which the average value of the vital data is calculated at the time of making the value-added information A. For example, the area may be a city, town, or village, or a block number. Also, it may be a geographical unit specified using a zip code, or the area that is set freely and have an arbitrary size.

Note that the value-added information B shows, using shading, the geographical distribution of the averages of the respective measurement values or the averages of the individual variations of the respective measurement values in the above-mentioned first and second embodiments, but such average values may by shown, for example, in a form of three-dimensional bar graph.

Note that it is described in the above-mentioned first and second embodiments that a measurement is automatically started in the measurement system 110 when a subject sits down on a toilet bowl, but the present invention is not limited to this. For example, it is the method that a subject operates a controller first, and orders the starts of the individual authentication and the check up.

Note that it is described in the above-mentioned first and second embodiments that the receiving apparatus set at the service destination is the PC 130, but it may be, for example, a mobile phone and a personal digital assistant (PDA) on condition that it has a communication function for receiving value-added information, a receipt and the like, and can output these data to an internal or external monitor or printer.

Figure 8:
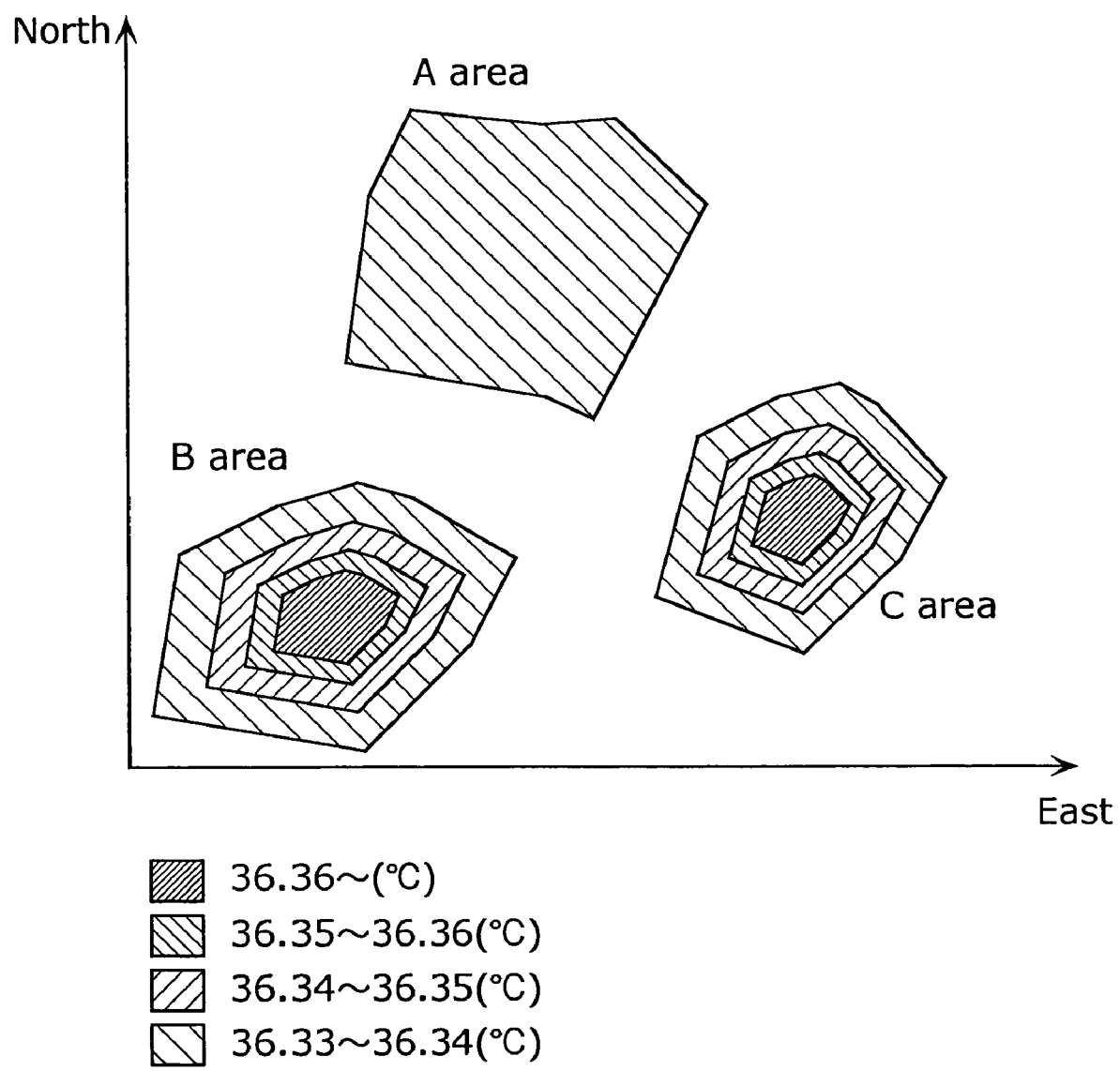
FIG. 8 is an example of value-added information B made by the value-added information making unit shown in FIG. 2.

Such a mobile phone that is the receiving apparatus of the present invention as mentioned above further has a function for detecting a present position such as a global positioning system (GPS) and issues a warning when a user moves in those four areas shown in the value-added information B of FIG. 8. Also, a present position may be displayed in the value-added information B using blinking. As patterns of issuing a warning, for example, the following patterns are conceivable: (i) a notification method notifying the infection level of each area (the epidemic degree of an infection in each area) each time a user enter each of the four areas, such a notification is made in a form of alarm sound, sound information, color display, animation display and the like; (ii) a notification method where stronger warning is issued to a user (in a form of alarm sound, sound information, color display, animation display and the like) each time the user enters the area where the epidemic level of an infection becomes higher than before (for example, the area where the average value of vital data such as body temperature becomes higher than before), in addition to this, in contrast, a notification method where a more comfortable notification (such as melody, effective sound, sound information, color display and animation display) is made to a user each time a user enters the area where the epidemic level of an infection becomes lower than before (the area where the average value of vital data such as body temperature becomes lower than before); and (iii) a notification method where a stronger warning is issued when a user moves to the direction of the epidemic center of an infection (the area where the average value of vital data such as body temperature is the highest) and where a more comfortable notification is made when the user moves to the direction opposite to the epidemic center of the infection, each time a present position is detected at a specific time intervals.

In order to realize the notification methods described above, more specifically, the user needs to obtain the value-added information B of FIG. 8 relating to the present position from the service provider first. Next, a mobile phone detects present positions every specific time (for example, every one minute, every 30 seconds or the like) using GPS or the like, and checks the detected present positions with the already-obtained value-added information B (the geographical distribution of vital data that is body temperature). This enables the mobile phone to identify the area where the user is present among the areas shown in the value-added information B and what the epidemic level (the degree of the average value of vital data that is body temperature) of the area is. In order to perform the notification method shown as (i), the mobile phone previously holds a table that shows notification types for the respective levels, checks the level of an identified area with the levels in the table, and issues a warning specified for the level of the identified area. Also, in order to execute the notification methods of (ii) and (iii), the mobile phone stores at least one pair of the area identified last and the vital data (body temperature) in the area. In this way, the mobile phone can judge whether or not the user enters the area closer to the epidemic center of an infection or whether the user moves to the direction of the epidemic center of the infection by comparing the level of the area where the user was present before and the level of the area to which the user moved. In this way, it is possible to issue a stronger warning when the user moves to the area where the user is more likely to face the danger of infection. Likewise, it is possible to issue a notification to the user in a form of more comfortable alarm sound or sound information when the user enters the area where the epidemic level of the infection becomes lower than before (the area where the average value of vital data that is body temperature becomes lower) or when the user moves to the direction opposite to the epidemic center of the infection.

Figure 12:
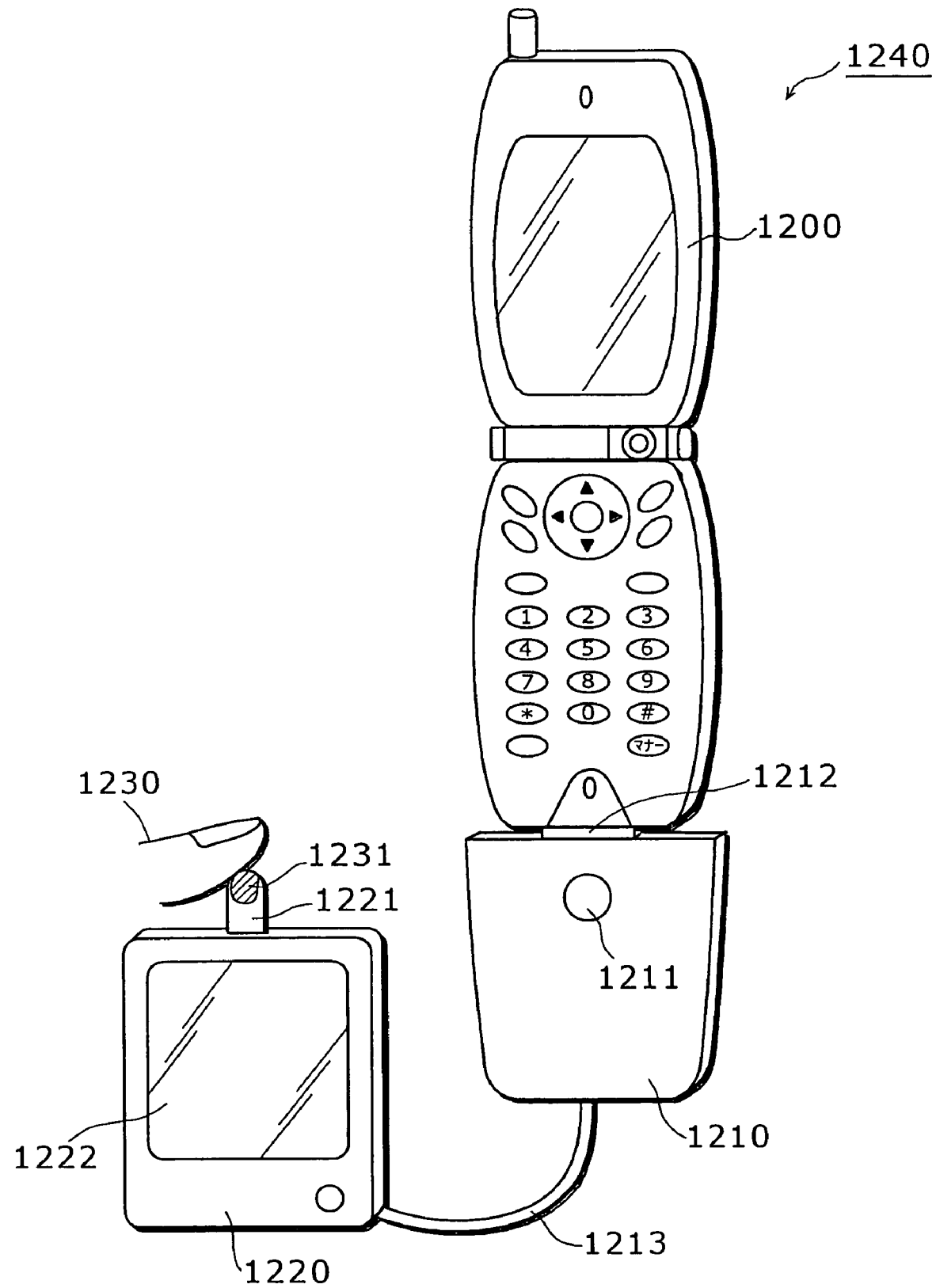
FIG. 12 is a diagram showing an example of the appearance of a conventional mobile phone that has a function for measuring vital data.

Also, the above-mentioned mobile phone that is the receiving apparatus of the present invention has a function as a mobile receiving apparatus, and can further have a function for sending vital data to the server 120 by becoming in combination with an existing measurement instrument and an existing communication adapter (such as a Glucocard diabetic meter made by Arkray Inc. and a mobile adapter). Note that the Glucocard diabetic meter made by Arkray Inc. is an instrument for measuring blood glucose level, but the measurement instrument of the present invention can be used for measuring not blood glucose level but the number of white blood cells, C-reactive protein and the like. FIG. 12 is a diagram showing one example of the appearance of the mobile measurement system 1240 that can have both functions as a measurement instrument and as a receiving apparatus by becoming in combination with an existing measurement instrument. The measurement system 1240 roughly includes a mobile phone 1200, a communication adapter 1210 and a measurement instrument 1220 that are detachable from each other. The mobile phone 1200 obtains the vital data to be sent to the server 120 from the communication adapter 1210 and sends it, receives value-added information from the server 120 and displays it on the monitor of the mobile phone 1200. The communication adapter 1210 includes a power supply button 1211, a connector 1212, a connection cable 1213 and the like. The power supply button 1211 is for turning on and off the power supply. The connector 1212 is the connection part for communicating the data with the mobile phone 1200. The connection cable 1213 is for transmitting, to the communication adapter 1210, the number of white blood cells and C-reactive protein and the like that are the measurement results by the measurement instrument 1220. The measurement instrument 1220 has a blood sensor 1221 and a display unit 1222. Blood 1231 taken through the finger 1230 of a subject is used as a sample, and the blood sensor 1221 measures, for example, the number of white blood cells or C-reactive protein in the sample. The display unit 1222 of the measurement instrument 1220 displays the number of measured white blood cells, C-reactive protein and the like. In this way, with the mobile measurement system 1240, the user can measure his/her own vital data outside and send it to the server 120, and also, the user can receive the distribution of the value-added information B from the server 120 outside and know the epidemic distribution of an infection outside. In this way, the user can take countermeasures such as taking care that he/she does not enter the area where an infection is epidemic when his/her physical fitness is not good and seeing a doctor in the hospital at an early opportunity.

Third Embodiment

Figure 13:
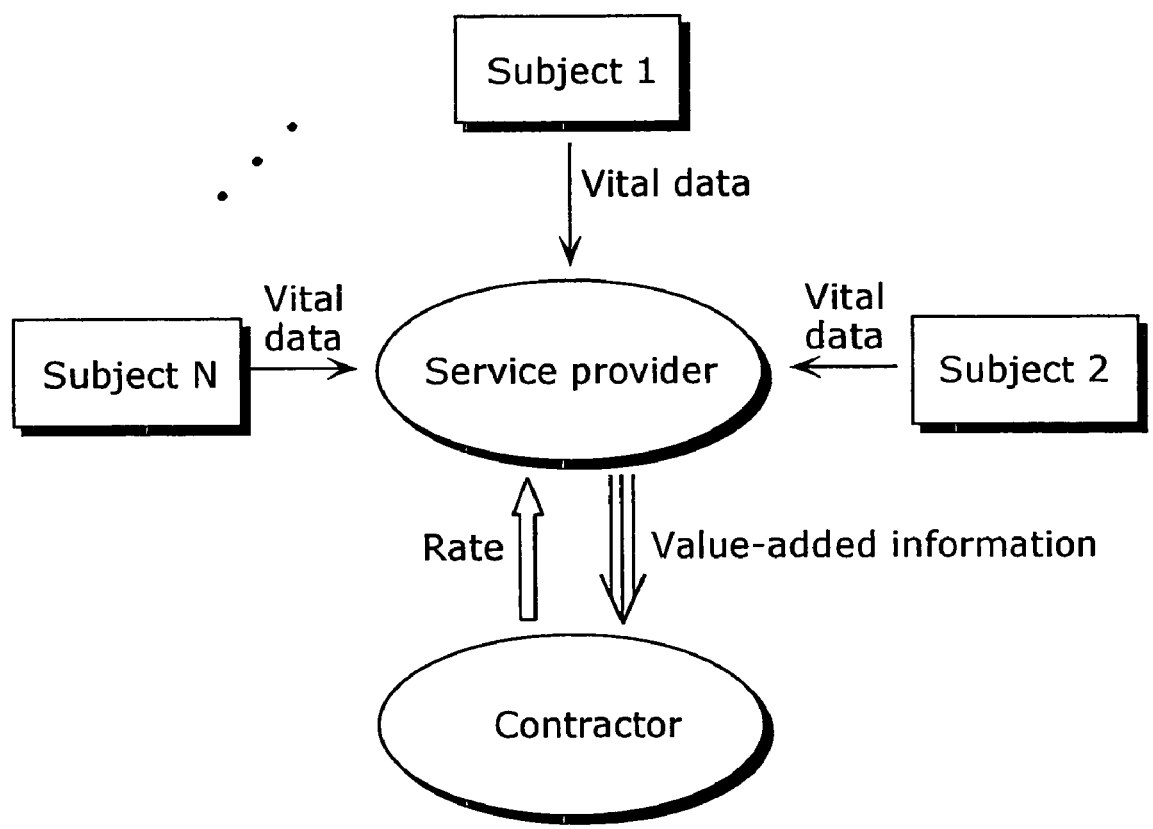
FIG. 13 is a diagram showing an example of data exchange in the vital data utilization system shown in FIG. 2.

The making method of value-added information in the present invention has already been described in the above-mentioned first and second embodiments, and in this third embodiment, an example method for providing the value-added information in the vital data utilization system of the present invention will be described with reference to FIGS. 2, 13, 14 and 15. FIG. 13 is a diagram showing one example of exchanging data in the vital data utilization system 100 shown in FIG. 2. Here is shown an example where respective subjects provide vital data to a service provider, but they do not contract as a service (value-added information) destination for the service provider. In the figure, a measurement system 110 shown in FIG. 2 is set in the respective subjects' (subjects 1 to N) homes. The vital data measured by the respective measurement systems 110 are sent to the service provider that has the server 120. The service provider makes the value-added information in the server 120 based on the vital data received from the subjects 1 to N, and distributes the made value-added information to the service destinations (the contractors) such as a medical institute, a public institute, a company and the like that have a PC 130 or the like. Also, the service provider charges the contractors that are the service businesses and the service destinations of the value-added information for the value-added information. The server 120 set at the service provider has a charging unit 124 inside, and the charging unit 124 calculates the charging amount on each contractor for the value-added information referring to the user information databases stored in the user information storage unit 127, and sends a bill to each PC 130 set at each service destination according to the calculation results.

Figure 14:
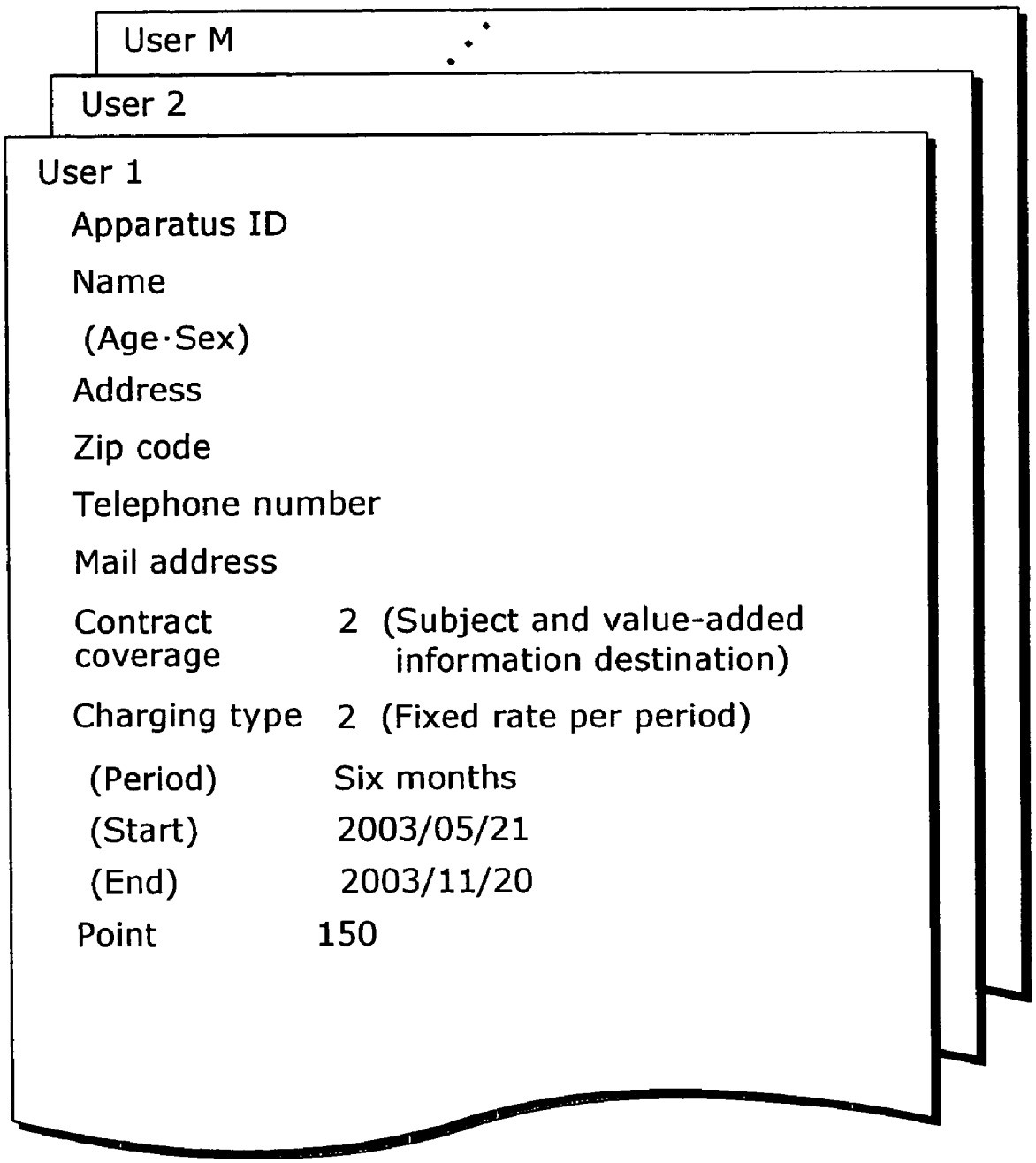
FIG. 14 is a diagram showing an example of user information database that is stored in the user information storage unit shown in FIG. 2.

FIG. 14 is a diagram showing one example of the user information database stored in the user information storage unit 127 shown in FIG. 2. As shown in the figure, the user information database is made for each user that is a contractor. In the user information database of each user, roughly, individual information on users and the contract coverage specified between the user and the service provider are described. More specifically, for example, the following articles are made for storing individual information on each user: user's apparatus ID; user's name (or the name of a company or the like in the case where the user is a group); user's age and sex (in the case where the user is an individual); user's address (the address of a company or the like in the case where the user is a group); user's zip code, user's telephone number, user's mail address and the like. The apparatus ID may be a unique ID issued to the user by the server 120 at the time of contracting, or it may be a uniform resource locator (URL). Either of them is used for sending/receiving the value-added information and vital data to/from each user.

Also, in the contract coverage described in the user information database of each user, articles such as contractor type, charging type, period, start, end, point are included. In the article of contractor type, a code indicating the relationship between the user and the service provider is described. For example, the code indicates that the contractor is simply a subject, the contractor is simply a service destination, or the contractor is a subject and a service destination. A code shows specific details, for example, it is possible to know the details by referring to a table that is not shown in any figure but previously stored in the user information storage unit. For example, in the figure, "2" is described as a code indicating a contract type. The contract type code 2 indicates that the user is a subject and a service destination. In the article of charging type, code 2 is described. The code 2 as the charging type indicates that the user makes the contract on a fixed-rate-per-period basis as a charging type. In the case where code 2 is described as the charging type, the articles of period, start and end are described. The length of the period for fixed rate charging such as "6 months" is described in the article of period, the start of the period for the fixed rate charging such as "21 May 2003" is described in the article of start, and the end of the period for the fixed rate charging such as "11 Nov. 2003" is described in the article of end. Also, in the article of point, in the case where the user is a contractor as a subject, the number of points stored for the user as an incentive to date is described.

Figure 15:
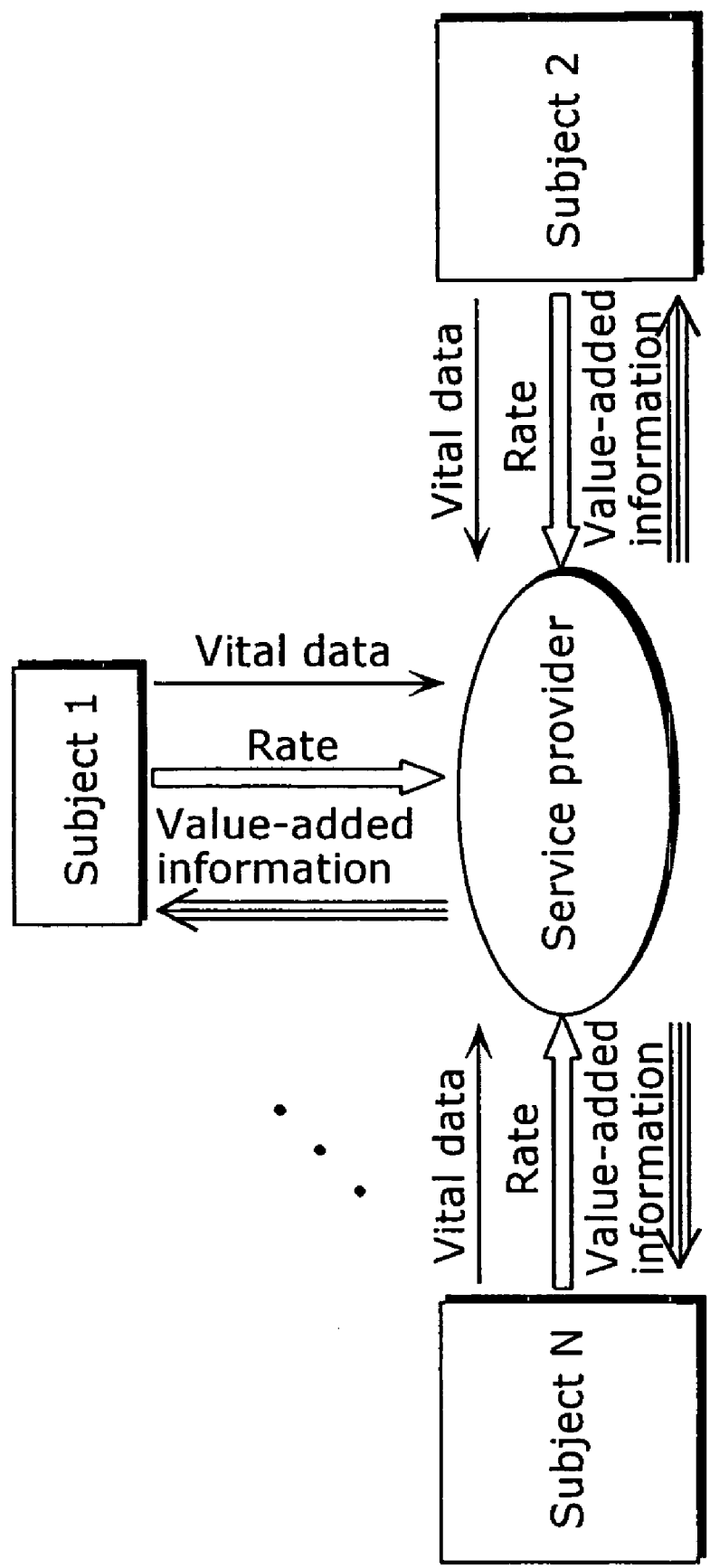
FIG. 15 is a diagram showing another example of data exchange in the vital data utilization system shown in FIG. 2.

FIG. 15 is a diagram showing another example of exchanging data in the vital data utilization system 100 shown in FIG. 2. Here is shown another example where the service destination is a subject. As shown in the figure, the vital data measured by the respective measurement systems 110 in the subjects' (subjects 1 to N) homes are sent to the service provider that has the server 120. The service provider makes the above-mentioned value-added information in the server 120 based on the vital data received from subjects 1 to N, and distributes the made value-added information to the service destination (contractor) that is the subject. Also, the service provider charges the subjects that are the service businesses and the service destinations of the value-added information. The server 120 set at the service provider has a charging unit 124 inside, and the charging unit 124 calculates the charging amount for each service destination for the value-added information referring to each user information database stored in the user information storage unit 127, and sends a bill to each measurement system 110 set at each subject's home according to the calculation result.

For example, the charging unit 124 calculates the charging amount for a user that is a service destination by referring to a table (not shown in any figure) where previously-set charging system is described. As examples, charging systems include: a measured rate system where rates are charged depending on the types and amount of provided value-added information; and a fixed rate per period system where fixed rates are charged depending on the length of the period but irrespective of the types and the amount of the provided value-added information. Further, the charging unit 124 manages the start and the end of the period in the case where the charging system is the fixed-rate-per-period system, and disables the communication unit 121 to distribute the value-added information to the user before and after the charging period. In this way described up to this point, with the charging unit 124, it is possible to charge the contractor that is the service destination for the value-added information for the distribution of value-added information.

Figure 16:
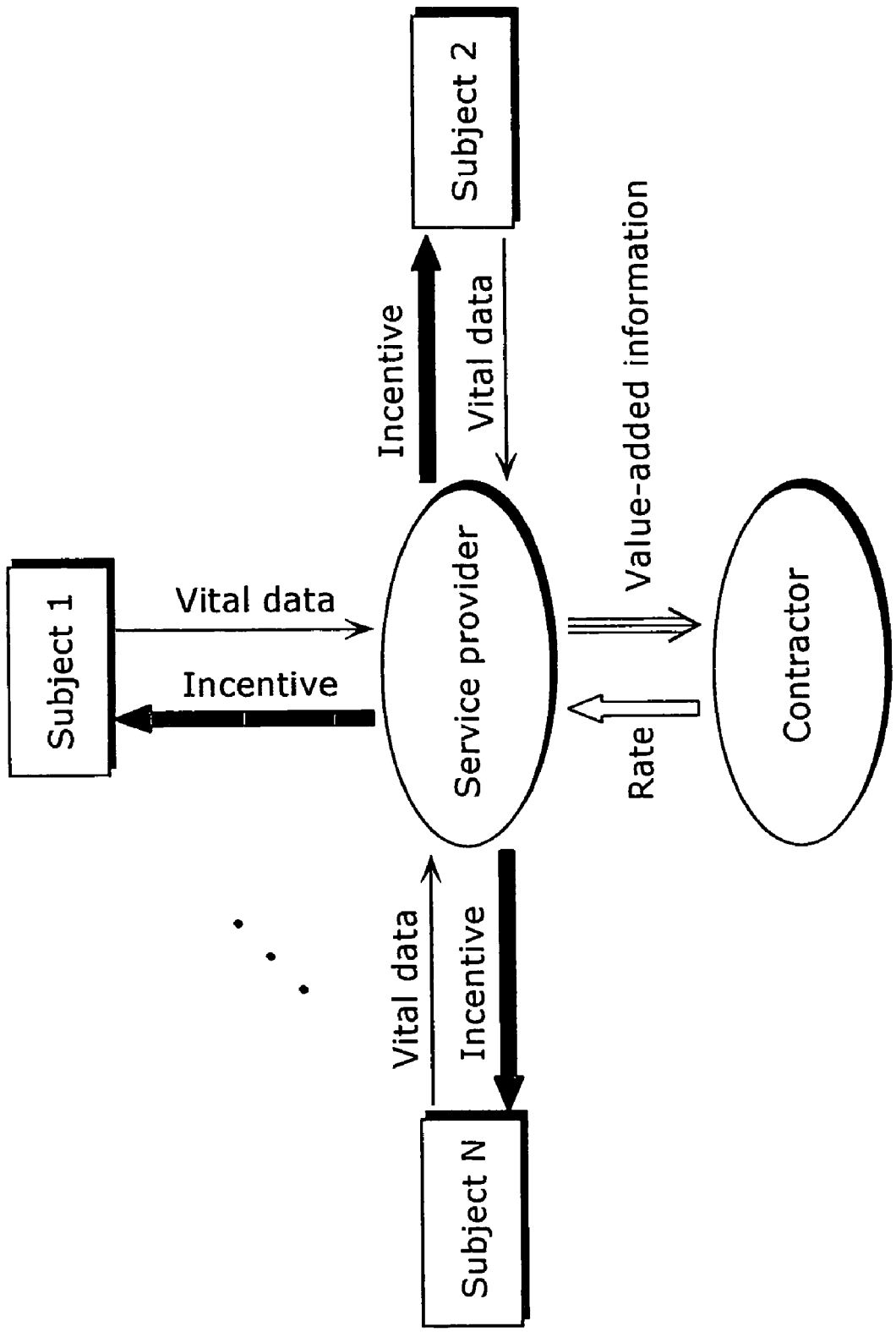
FIG. 16 is a diagram showing another example of data exchange in the vital data utilization system shown in FIG. 2.

Further, in the present invention, in the case where a subject makes a point of measuring vital data periodically and continuously and sending the vital data that is the measurement results, it becomes possible to enhance the effectiveness of the value-added information more. Aiming at this, for example, it is possible to provide an incentive for sending the vital data to the subject periodically and continuously. FIG. 16 is a diagram showing another example of exchanging data in the vital data utilization system 100 shown in FIG. 2. Here is shown an example where the service provider provides each subject with an incentive. An incentive calculation unit 125 set in the server 120 shown in FIG. 2 issues a predetermined number of points to the subject who has sent his/her vital data more than a predetermined times in a certain time zone of a certain period.

The incentive calculation unit 125, manages the rights to be issued depending on the number of points that are stored after calculating points of the respective subjects with reference to the table that is previously stored in the user information storage unit 127. For example, the incentive calculation unit 125 refers to individual vital data databases for the respective subjects and provides incentives of (i) 5 points to the user who has measured his/her vital data once within the range of one hour over a month and sends the sets of vital data to the server 120, (ii) 20 points to the user who has measured his/her vital data once within the range of one hour over three months and sends the sets of vital data to the server 120, and (iii) 50 points to the user who has measured his/her vital data once within the range of one hour over six months and sends the sets of vital data to the server 120. The incentive calculation unit 125 updates articles of points in the user information databases based on the statuses of how the respective subjects continuously send his/her vital data.

Also, the incentive calculation unit 125 issues a right as mentioned above when the number of points that are issued and stored for each user exceeds a certain number. In the case where 20 points or more are stored for each subject, the incentive calculation unit 125 issues a right such as the right to receive a 10-percent discount from the charge for value-added information and the right to receive a 10-percent discount from the price of a reagent for a check-up or the like according to each user's selection. In the case where a user selects receiving the right of a discount from the charge, the discount rate is notified to the charging unit 124. In the case where a user selects receiving the right of a discount from the price of a test reagent, for example, printing processing and the like for issuing a discount ticket and the like using mail are performed. In this way, in the case where a subject consumes his/her points by receiving a discount from the charge for value-added information or a discount from the price of a test reagent, the incentive calculation unit 125 subtracts the consumed points from the total points stored for the subject and updates the article of point in the user information database. In this way, the incentive calculation unit 125 calculates the points of the respective subjects based on the periodicity and the continuity of measuring vital data. This produces an effect that high-quality vital data can be collected more effectively.

Also, the number of incentive points may be added, for example, based on the amount of vital data stored in each individual vital data database. In this way, in the case where points are added based on the amount of stored vital data, points are calculated irrespective of whether or not sets of vital data are measured at a constant time, however, it is possible to encourage the user to measure his/her vital data continuously for a long period and moreover, the effect of reducing the calculation load of the incentive calculation unit 125 can be obtained.

Figure 17:
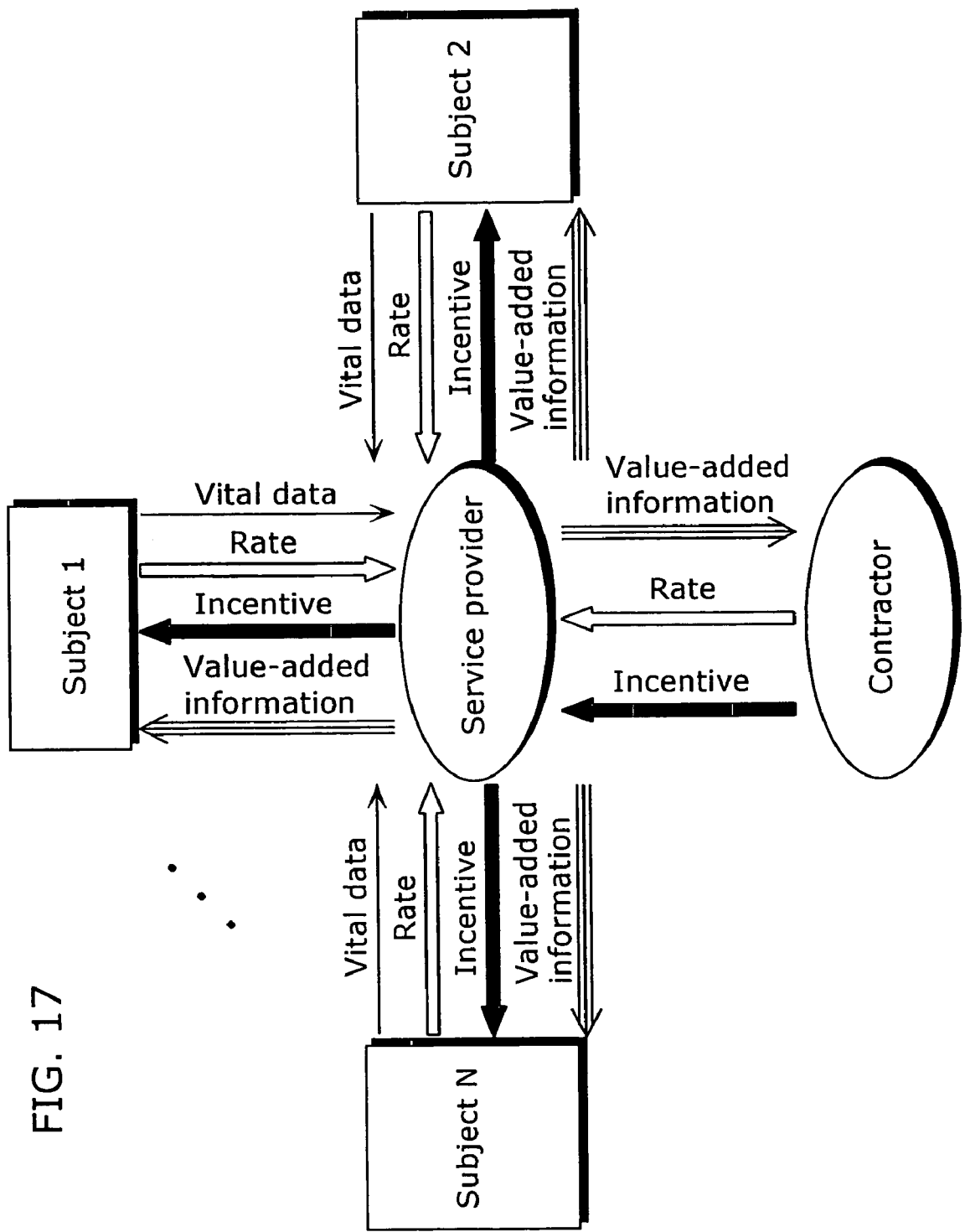
FIG. 17 is a diagram showing still another example of data exchange in the vital data utilization system shown in FIG. 2.

Note that an example where the service provider provides an incentive to subjects is shown in FIG. 16, but the service provider may only calculate the incentives and the contractor may provide an incentive to the subjects. FIG. 17 is a diagram showing another example of exchanging data in the vital data utilization system 100 shown in FIG. 2. Here, the service (value-added information) destinations by the service provider are the contractors and subjects such as a medical institute, a public institute and a company. In this case, the incentive calculation unit 125 calculates the amount corresponding to the issued incentives and notifies the charging unit 124 of the amount. The charging unit 124 distributes the notified amount of rate to the contractors except subjects and adds the amount to the rates. In this case, the service destination that is the user side of value-added information gives incentives for collecting higher-quality vital data and receiving higher-quality value-added information.

Note that a discount from the rate for value-added information, a discount from the price of a test reagent or the like that is used in the measurement unit 111, a right to receive exchange and the like are listed as an incentive in the above-mentioned embodiment, but other than that, it may be a right to receive a commodity such as a detergent or a discount from the rate for a service of some kind.

Also, various providing method of value-added information have already been described in the above-mentioned embodiment with reference to FIG. 13 to FIG. 17, but the present invention is not limited to this, and it is possible to use such providing methods in combination as deemed appropriate.

Note that the present invention can be realized not only as the measurement system 110, the toilet apparatus 200 and the server 120 alone but also as a vital data utilization system including the measurement system 110, the server 120, the PC 130 and the like, and a program causing a computer to function a part of or all of the processing units included in the measurement system 110 and the server 120. In addition, such a program can be widely distributed via a recording medium such as a CD-ROM or the like and a communication medium such as the Internet.

Also, the above-mentioned program may cause a computer to execute a part of or all of the vital data utilization method of the present invention, cause a computer to control the machine operation units such as the measurement unit, and cause the machine operation units to function in association with the computer.

Also, the recording medium of the present invention has a program for causing a computer to execute a part of or all of the functions in a part of or all of the steps (or processes, operations, actions or the like) of the vital data utilization method of the above-mentioned present invention. The recording medium can be read by a computer and allow the operations of the read program to be executed in concert with the computer.

Note that "a part of steps (or processes, operations, actions or the like)" of the present invention means one or several steps among these steps.

Also, "functions of steps (or processes, operations, actions or the like)" of the present invention means a part of or all of the functions of the steps.

Also, a use form of the program in the present invention may be the form that is recorded in a computer-readable recording medium and functions in concert with a computer.

Also, another use form of the program in the present invention may be the form that is transmitted via a transmission medium, that is read by a computer and functions in concert with a computer.

Also, the data structures of the present invention include a database, a data format, a data table, a data list, a data type and the like.

Also, recording media include a ROM and the like, and communication media include the Internet, light, a radio wave, a sound wave and the like.

Also, the above-mentioned computer of the present invention is not limited to hardware such as a CPU, and it may be the one that also includes firmware, an OS, and further a peripheral apparatus.

Note that, as described up to this point, the structure of the present invention may be realized in a form of both software and hardware.

INDUSTRIAL APPLICABILITY

The measurement instrument in the present invention is useful for housing equipment such as a toilet apparatus and a bed, and sanitary apparatus such as a toilet apparatus that is set at a public facility.

Also, the receiving apparatus in the present invention is useful for a personal computer, a PDA, a car navigation apparatus and a mobile phone and the like that have a communication function.

The invention claimed is:

1. A vital data utilization system comprising:
   a server;
   a receiving apparatus; and
   a plurality of measurement instruments,
   wherein said server, said receiving apparatus and said measurement instruments are connected via a communication network,
   wherein each of said measurement instruments includes:
      a vital data measurement device that measures a body temperature of a respective subject; and
      a sending device that sends the measured body temperature to said server,
   wherein said server includes:
      a receiving device that receives a plurality of measured body temperatures from said plurality of measurement instruments;
      a storage device that stores each of the plurality of body temperatures, each of the plurality of body temperatures being stored in association with residence information indicating a position of a respective residence of the subject at which a respective measurement instrument included in said plurality of measurement instruments is placed;

a database making device that stores the plurality of body temperatures into said storage device to make a database including the plurality body temperatures, each of the plurality of body temperatures being included in the database in association with the residence information;

a value-added information making device that calculates, for each respective area of a plurality of areas, an average value of the plurality of body temperatures, based on (a) the plurality of body temperatures of the subjects and (b) the residence information associated with the plurality of body temperatures, and makes, from the plurality of body temperatures included in the database, value-added information indicating a geographical distribution of average values of the plurality of body temperatures calculated for the respective areas using shading such that the shading becomes darker as the average values increase and such that the shading becomes lighter as the average values decrease; and a value-added information providing device that provides said receiving apparatus with the value-added information, and wherein said receiving apparatus includes an output device that receives the value-added information provided by said value-added information providing device, and presents and outputs the geographical distribution of the average values of the plurality of body temperatures, such that the geographical distribution is superimposed on a map, the geographical distribution representing the average values using shading such that the shading becomes darker as the average values increase and such that the shading becomes lighter as the average values decrease.

2. The vital data utilization system according to claim 1, wherein each measurement instrument included in said plurality of measurement instruments further includes a clock device that detects a measurement time at which the body temperature is measured, wherein said sending device sends, to said server, a set of information including the body temperature and the measurement time, wherein said receiving device of said server receives a plurality of sets of information from said plurality of measurement instruments, wherein said storage device of said server stores the plurality of sets of information, each respective set of information of the plurality of sets of information including a respective body temperature and a respective measurement time and each respective set of information being stored in association with the residence information, wherein said database making device of said server stores the plurality of received sets of information into said storage device to make a database including the plurality of received sets of information, each respective set of information being included in the database in association with the residence information, and wherein said value-added information making device of said server processes the body temperature of each respective set of information included in the database for the respective subject identified in the database in association with a respective measurement time and makes, from the body temperatures included in the database for each subject identified in the database in association with the respective measurement time, value-added information indicating changes over time of a geographical distribution of the average values indicated by the plurality of body temperatures included in the database, the geographical distribution representing the changes over time of the average values using shading such that the shading becomes darker as the average values increase and such that the shading becomes lighter as the average values decrease.

3. The vital data utilization system according to claim 1, wherein said vital data measurement device quantitatively measures the subjects' body temperatures.

4. The vital data utilization system according to claim 1,
wherein said sending device adds, to a plurality of respective sets of information, respective information including a respective body temperature and respective measurement instrument identification information identifying a corresponding measurement instrument and sends the respective sets of information including the respective measurement identification information to said server, wherein said storage device stores the plurality of sets of respective information, each respective set of information including the body temperature and respective measurement instrument identification information and each respective set of information being stored in association with the residence information, wherein said value-added information making device reads out, from said storage device, the residence information, based on the measurement instrument identification information received from the server, and processes the body temperature based on at least one of the read-out information.

5. The vital data utilization system according to claim 1,
wherein said sending device adds, to a plurality of respective sets of information, respective information including a respective body temperature, and the residence information, and sends the plurality of respective sets of information to said server, and wherein said value-added information making device processes the body temperature of each respective set of information received from said sending unit, based on the residence information received from said sending device.

6. The vital data utilization system according to claim 1,
wherein said database making device updates the database each time at least one new set of information including the body temperature is received, and wherein said value-added information making device updates the value-added information based on the updated database.

7. The vital data utilization system according to claim 1, wherein said receiving apparatus is placed in at least one of a hospital, a public facility excluding a hospital, and a house of the subject.

8. The vital data utilization system according to claim 1, wherein said vital data measurement device is located at housing equipment in a house of the subject.

9. The vital data utilization system according to claim 8,
wherein the housing equipment is one of a toilet apparatus and a bed, and wherein said vital data measurement device includes a thermometer for measuring the body temperature, and said vital data measurement device measures the body temperature at a time when the subject uses one of the toilet apparatus and the bed.

10. The vital data utilization system according to claim 1, wherein said server further includes a charging device that calculates a charge for value-added information provided to said receiving apparatus.

11. The vital data utilization system according to claim 10, wherein said server further includes an incentive calculation device that calculates an incentive for each subject.

12. The vital data utilization system according to claim 11, wherein said incentive calculation device adds, to a charge calculated by said charging device, a value of the incentive for each subject.

13. The vital data utilization system according to claim 11, wherein said incentive calculation device calculates points to be exchanged for at least one of (i) a right to receive the value-added information, (ii) a right to receive a discount from a rate of the value-added information, (iii) a right to receive a free distribution of or a discount from a sale price of a commodity to be used by said vital data measurement device, (iv) a right to receive another service, and (v) a right to receive a free distribution of or a discount from a sale price of another commodity.

14. The vital data utilization system according to claim 1, wherein said receiving apparatus is a mobile type apparatus and further includes a present position detection device that detects a present position, and
wherein said output device receives the value-added information indicating the geographical distribution of the average values of the plurality of body temperatures of the respective subjects located at the detected present position and located at a peripheral part of the detected present position, and presents and outputs the geographical distribution of the average values of the plurality of body temperatures of the respective subjects located at the detected present position and located at the peripheral part of the detected present position, the geographical distribution representing the average values of the plurality of body temperatures using shading such that the shading becomes darker as the average values increase and such that the shading becomes lighter as the average values decrease, the value-added information being provided by said value-added information providing device.

15. A server in a system in which said server, a receiving apparatus and a plurality of measurement instruments are connected via a communication network, said server comprising:
a receiving device that receives a plurality of body temperatures from the plurality of measurement instruments;
a storage device that stores the plurality of body temperatures, each of the plurality of body temperatures being stored in association with residence information indicating a position of a respective residence of a subject at which a respective measurement instrument included in the plurality of measurement instruments is placed;
a database making device that stores the plurality of body temperatures into said storage device to make a database including the plurality of body temperatures, each of the plurality of body temperatures being included in the database in association with the residence information;
a value-added information making device that calculates, for each respective area of a plurality of areas, an average value of the plurality of body temperatures, based on (a) the plurality of body temperatures of the subjects and (b) the residence information, associated with the plurality of body temperatures, and makes, from the plurality of body temperatures included in the database for each subject identified in the database in association with the respective measurement time, value-added information indicating a geographical distribution of average values of the plurality of body temperatures or changes over time of the geographical distribution of the average values of the plurality of body temperatures, the geographical distribution representing the average values calculated for the respective areas and the changes over time of the average values using shading such that the shading becomes darker as the average values increase and such that the shading becomes lighter as the average values decrease; and
a value-added information providing device that provides the receiving apparatus with the value-added information.

16. The server according to claim 15,
wherein said receiving device receives, from each respective measurement instrument, a respective set of information to which measurement instrument identification information identifying the respective measurement instrument is added,
wherein said storage device previously stores the residence information, and
wherein said value-added information making device reads out, from said storage device, the residence information, based on the received measurement instrument identification information, and calculates the average value of the plurality of body temperatures in each area based on at least one of the read-out information.

17. The server according to claim 15,
wherein said receiving device receives, from each respective measurement instrument, a respective set of information to which the residence information is added, and
wherein said value-added information making device calculates the average value of the plurality of body temperatures in each area based on at least one of (i) the measurement instrument position information and (ii) the received residence information.

18. The server according to claim 15,
wherein said database making device updates the database each time at least one new set of information including the body temperature is received, and
wherein said value-added information making device updates the value-added information based on the updated database.

19. A vital data utilization method of using a system in which a server, a receiving apparatus, and a plurality of measurement instruments are connected via a communication network, said vital data utilization method comprising:
using each respective measurement instrument for:
measuring a body temperature of a respective subject; and
sending the measured body temperature to the server;
using the server, including a storage device that stores a plurality of body temperatures, each of the plurality of body temperatures being stored in association with residence information indicating a position of a respective residence of the subject at which a respective measurement instrument included in the plurality of measurement instruments is placed, for:
receiving the plurality of body temperatures from the plurality of measurement instruments;
storing the plurality of body temperatures into the storage device to make a database including the plurality of body temperatures, each of the plurality of body temperatures being stored in association with the residence information;

calculating, for each respective area of a plurality of areas, an average value of the plurality of body temperatures, based on (a) the plurality of body temperatures of the subjects and (b) the residence information, associated with the plurality of body temperatures, and making, from the plurality of body temperatures included in the database for each subject identified in the database in association with the respective measurement time, value-added information indicating a geographical distribution of average values of the plurality of body temperatures included in the database or changes over time of the geographical distribution of the average values of the plurality of body temperatures included in the database, the geographical distribution representing the average values of the plurality of body temperatures calculated for the respective areas of the plurality of areas and the changes over time of the average values using shading such that the shading becomes darker as the average values increase and such that the shading becomes lighter as the average values decrease; and providing the receiving apparatus with the value-added information; and using the receiving apparatus for receiving the value-added information provided in said providing, and presenting and outputting the geographical distribution of the average values of the plurality of body temperatures, such that the geographical distribution is superimposed on a map, the geographical distribution representing the average values calculated for the respective areas and the changes over time of the average values using shading, such that the shading becomes darker as the average values increase and such that the shading becomes lighter as the average values decrease.

20. A vital data utilization method of using a server in a system in which the server, a receiving apparatus, and a plurality of measurement instruments are connected via a communication network, the server including a storage device that stores a respective body temperature in association with residence information indicating a position of a respective residence of a subject at which a respective measurement instrument included in the plurality of measurement instruments is placed, said vital data utilization method comprising:

receiving a plurality of body temperatures from the plurality of measurement instruments;

storing the received plurality of body temperatures in association with the residence information, to make a database including, as a plurality of received sets of information, the received plurality of body temperatures;

calculating, for each respective area of a plurality of areas, an average value of the plurality of body temperatures, based on (a) the plurality of body temperatures of subjects and (b) the residence information, associated with the plurality of body temperatures, and making value-added information indicating a geographical distribution of average values of the plurality of body temperatures included in the database or changes over time of the geographical distribution of the average values of the plurality of body temperatures included in the database, the geographical distribution representing the average values calculated for the respective areas and the changes over time of the average values using shading such that the shading becomes darker as the average values increase and such that the shading becomes lighter as the average values decrease; and providing the receiving apparatus with the value-added information.

21. A computer-readable recording medium having a program recorded thereon, the program causing a computer to execute a method comprising:

receiving a plurality of body temperatures from a plurality of measurement instruments;

storing the received plurality of body temperatures into the storage device to make a database including the plurality of body temperatures, each of the plurality of body temperatures being stored in association with residence information indicating a position of a respective residence of a respective subject at which a respective measurement instrument included in the plurality of measurement instruments is placed;

calculating, for each respective area of a plurality of areas, an average value of the plurality of body temperatures, based on (a) the plurality of body temperatures of subjects and (b) the residence information, associated with the plurality of body temperatures, and making, from the plurality of body temperatures included in the database for each subject identified in the database in association with the respective measurement time, value-added information indicating a geographical distribution of average values of the plurality of body temperatures included in the database or changes over time of the geographical distribution of the average values of the plurality of body temperatures included in the database, the geographical distribution representing the average values calculated for the respective areas of the plurality of areas and the changes over time of the average values using shading such that the shading becomes darker as the average values increase and such that the shading becomes lighter as the average values decrease; and providing the receiving apparatus with the value-added information.

22. A receiving apparatus in a system in which a server, said receiving apparatus and a plurality of measurement instruments are connected via a communication network, said receiving apparatus comprising an output device that receives information provided by the server, and presents and outputs the received information, wherein each of the measurement instruments includes:
a vital data measurement device that measures a body temperature of a respective subject; and
a sending device that sends the measured body temperature to the server, wherein the server includes:
a receiving device that receives a plurality of measured body temperatures from the plurality of measurement instruments;
a storage device that stores the plurality of body temperatures, each of the plurality of body temperatures being stored in association with residence information indicating a position of a respective residence of the subject at which a respective measurement instrument included in the plurality of measurement instruments is placed;
a database making device that stores the plurality of body temperatures into the storage device to make a database including the plurality of body temperatures, each of the plurality of body temperatures being included in the database in association with the residence information;

a value-added information making device that calculates, for each respective area of a plurality of areas, an average value of the plurality of body temperatures, based on (a) the plurality of body temperatures of the subjects and (b) the residence information, associated with the plurality of body temperatures, and makes, from the plurality of body temperatures included in the database for each subject identified in the database in association with the respective measurement time, value-added information indicating a geographical distribution of average values of the plurality of body temperatures included in the database or changes over time of the geographical distribution of the average values of the plurality of body temperatures included in the database, the geographical distribution representing the average values calculated for the respective areas of the plurality of areas and the changes over time of the average values using shading such that the shading becomes darker as the average values increase and such that the shading becomes lighter as the average values decrease; and a value-added information providing device that provides said receiving apparatus with the value-added information; and wherein said output device receives the value-added information provided by the value-added information providing device, and presents and outputs the geographical distribution of the average values of the plurality of body temperatures included in the database or the changes over time of the geographical distribution of the average values of the plurality of body temperatures included in the database, such that the geographical distribution is superimposed on a map, the geographical distribution representing the average values calculated for the respective areas of the plurality of areas and the changes over time of the average values using shading such that the shading becomes darker as the average values increase and such that the shading becomes lighter as the average values decrease.

23. The receiving apparatus according to claim 22, the receiving apparatus being a mobile type apparatus and further comprising a present position detection device that detects a present position, wherein said output device receives the value-added information indicating the geographical distribution of the average values of the plurality of body temperatures of the respective subjects located at the detected present position and located at a peripheral part of the detected present position, and presents and outputs the geographical distribution of the average values of the plurality of body temperatures of the respective subjects located at the detected present position and located at the peripheral part of the detected present position, such that the geographical distribution is superimposed on a map, the geographical distribution representing the average values using shading such that the shading becomes darker as the average values increase and such that the shading becomes lighter as the average values decrease.

* * * * *